United States Patent [19]

Rink et al.

[11] 4,238,481
[45] Dec. 9, 1980

[54] NOVEL CYCLOPEPTIDES

[75] Inventors: Hans Rink, Riehen; Bruno Kamber, Arlesheim; Peter Sieber, Reinach, all of Switzerland

[73] Assignee: Ciba-Geigy Corporation, Ardsley, N.Y.

[21] Appl. No.: 942,565

[22] Filed: Sep. 15, 1978

[30] Foreign Application Priority Data

Sep. 28, 1977 [LU] Luxembourg ............................ 78191

[51] Int. Cl.³ ..................... A61K 37/00; C07C 103/52
[52] U.S. Cl. ................................. 424/177; 260/112.55
[58] Field of Search ..................... 424/177; 260/112.55

[56] References Cited

U.S. PATENT DOCUMENTS

| | | | |
|---|---|---|---|
| 3,988,304 | 10/1976 | Garsky | 260/112.5 S |
| 4,000,259 | 12/1976 | Garsky | 260/112.5 S |
| 4,054,558 | 10/1977 | Garsky | 260/112.5 S |
| 4,115,554 | 9/1978 | Veber | 424/177 |
| 4,146,612 | 3/1979 | Veber | 424/177 |

FOREIGN PATENT DOCUMENTS

| | | | |
|---|---|---|---|
| 2635558 | 8/1976 | Fed. Rep. of Germany | 260/112.5 S |
| 7602793 | 3/1975 | Netherlands | 260/112.5 S |

OTHER PUBLICATIONS

J.A.C.S. 98, 1976, pp. 2367–2369.

Primary Examiner—Delbert R. Phillips
Attorney, Agent, or Firm—John J. Maitner; Prabodh I. Almaula

[57] ABSTRACT

Sulphur-free cyclopeptides with somatostatin-analogous aminoacid partial sequences, of the formula

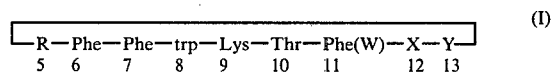

$$\begin{array}{cccccccc} \text{—R—Phe—Phe—trp—Lys—Thr—Phe(W)—X—Y—} \\ 5 & 6 & 7 & 8 & 9 & 10 & 11 & 12 & 13 \end{array} \quad (I)$$

in which R is Asn, Ala or de-R, trp is D-Trp or L-Trp, which can be substituted in the benzene ring by halogen atoms or nitro groups, W is a free or etherified hydroxyl group or halogen atom present as a substituent on the benzene ring of the L-phenylalanine radical, or is hydrogen, X is the radical of an ω-amino-lower alkane-(mono or di)-carboxylic acid or de-X and Y is the radical of an ω-amino-lower alkane-(mono or di)-carboxylic acid or de-Y, and also acid addition salts and complexes thereof have biological properties similar to those of somatostatin and can be used, especially in the form of pharmaceutical preparations, for the treatment of excessive secretion of somatotropin, insulin and/or glucagon. The compounds according to the invention are obtained by cyclising a corresponding linear peptide compound in which the ε-amino group of the lysine radical and, if desired, also the hydroxyl group of the threonine radical are protected and detaching the protective groups which are present.

10 Claims, No Drawings

NOVEL CYCLOPEPTIDES

The invention relates to novel cyclopeptides of the somatostatin type and processes for their preparation and also to pharmaceutical preparations containing these compounds and the use of these compounds and preparations for therapeutic purposes.

The invention relates especially to cyclopeptides which contain the most essential characteristics of somatostatin, such as the partial sequence of aminoacids 5-11, or an equivalent sequence, but are sulphur-free. The somatostatin-analogous cyclopeptides according to the invention comprise compounds of the formula

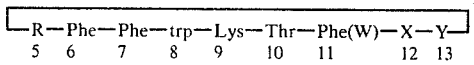
(I)

in which R is Asn, Ala or de-R, trp is D-Trp or L-Trp, which can be substituted in the benzene ring by halogen atoms, such as, in particular, chlorine or fluorine, or nitro groups, W is a free or etherified hydroxyl group or halogen atom, such as, in particular, an iodine atom, present as a substituent on the benzene ring of the L-phenylalanine radical, or is hydrogen, X is the radical of an ω-amino-lower akane-(mono or di)-carboxylic acid or de-X and Y is the radical of an ω-amino-lower alkane-(mono or di)-carboxylic acid or de-Y, and also acid addition salts and complexes thereof.

The halogen atoms which may be present in the benzene ring of the tryptophan[8] radical are preferably in the 5-position and the nitro group is preferably in the 6-position; particularly preferred radicals are those derived from 5-bromo-L-tryptophan, 5-fluoro-D-tryptophan and 6-nitro-D-tryptophan. The substituent W of the L-phenylalanine[11] radical is preferably in the p-position of the benzene ring; in addition to the unsubstituted L-phenylalanine radical, the p-iodo-L-phenylalanine and p-hydroxy-L-phenylalanine radical are also particularly preferred. The hydroxyl group of the latter radical (i.e. of the L-tyrosine radical) can also be in an etherified form; lower alkyls and also various ether-forming hydroxyl protective groups customary in peptide chemistry, for example those mentioned further below, are suitable for this purpose; the tert.-butyl group is particularly preferred and the preferred aminoacid[11] radical is derived from p-tert.-butoxyphenylalanine (i.e. tyrosine tert.-butyl ether).

The radical of an ω-amino-lower alkane-monocarboxylic acid is preferably a radical of the formula —NH—(CH$_2$)$_n$—CO— in which n is an integer from 1 to 7, especially 2-4. The radical of γ-amino-butyric acid, which is designated by the symbol Gaba, is particularly preferred.

The radical of an ω-amino-lower alkane-dicarboxylic acid is preferably derived from a radical of the formula

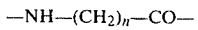

in which n is as defined above and the carboxyl group can also be in a functionally modified form, for example in the form of an ester or amide, such as an ester customary in peptide chemistry or an unsubstituted amide. A radical of L- or especially of D-glutamic acid of the formula

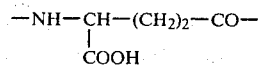

or a corresponding radical in which the carbamoyl group is present in place of the carboxyl group, is particularly preferred.

In accord with the conventional use in nomenclature, the prefix "de" signifies that a symbol designated in this way is lacking; thus, for example, the term "de-X" denotes that the symbol X has the meaning [X]$_m$ in which m=0 and is to be omitted from the corresponding formula.

The preferred somatostatin analogues according to the invention are those in which R is preferably Asn or de-R, the tryptophan[8] radical has the D-configuration and -X-Y- together are -[Gaba]$_p$-, in which p is 0, 1 or 2. Particularly preferred compounds are those of the formula

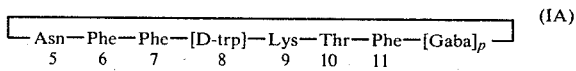
(IA)

in which p is 2 or, in particular, p is 1. All of these preferred somatostatin analogues can also be in the form of acid addition salts or complexes.

Acid addition salts are, in particular, physiologically acceptable salts with conventional therapeutically usable acids; the inorganic acids include the hydrogen halide acids, such as hydrochloric acid, but also sulphuric acid and phosphoric and pyrophosphoric acid, and the organic acids are, in particular, the sulphonic acids, such as benzenesulphonic acid or p-toluenesulphonic acid, or lower alkanesulphonic acids, such as methanesulphonic acid, and also carboxylic acids, such as acetic acid, lactic acid, palmitic acid and stearic acid, malic acid, tartaric acids, ascorbic acid and citric acid.

Complexes are to be understood as meaning compounds for which the structure has not yet been completely clarified and which are formed on adding certain inorganic or organic substances to peptides and impart a longerlasting action to the latter. Such substances have been described, for example, for ACTH and other peptides having an adrenocorticotropic action. Specific substances are, for example, inorganic compounds which are derived from metals such as calcium, magnesium, aluminium and cobalt and especially from zinc, in particular sparingly soluble salts, such as phosphates, pyrophosphates and polyphosphates, and also hydroxides, of these metals, and also alkali metal polyphosphates, for example "Calgon N", "Calgon 322", "Calgon 188" or "Polyron B 12". Organic substances which prolong the action are, for example, non-antigenic types of gelatine, for example polyoxygelatine, polyvinylpyrrolidone and carboxymethylcellulose, and also sulphonates or phosphates of alginic acid, dextran, polyphenols and polyalcohols, in particular polyphloretin phosphate and phytic acid, and also polymers and copolymers of basic or, in particular, acid aminoacids, for example protamine or polyglutamic acid.

Unless otherwise stated, the term "lower" used to qualify an organic radical or compound denotes that such a radical or compound contains not more than 7, but preferably not more than 4, carbon atoms.

The novel cyclopeptides according to the invention have a physiological action which in character and intensity is equivalent to the action of somatostatin. They can therefore advantageously be used in therapeutic indications similar to those for somatostatin, for example for the treatment of functional disorders, in which the secretion of the growth hormone or of insulin and glucagon is abnormally high, such as in acromegalia or juvenile diabetes.

As is known, somatostatin, which is a cyclic tetradecapeptide of the formula

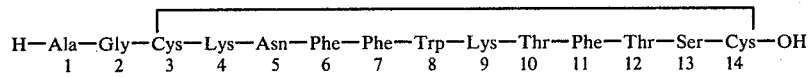

[Science 179, 77 (1973)] inhibits the hypophyseal-controlled secretion of the growth hormone (somatotropin). In addition it inhibits the secretory activity of the endocrine pancreas, such as the secretion of insulin and glucagon.

In the case of somatostatin itself, these valuable characteristics are not able to be put to full practical use, since the complex chemical structure of this compound stands in the way of its industrial synthesis. In addition to the large number of aminoacids, the presence of cystine is also particularly disadvantageous: because of its sulphur content, this aminoacid prevents the use of the extremely advantageous protective groups detachable by hydrogenolysis. Moreover, half (7 out of 14) of the aminoacids of somatostatin have further functional groups in the side chain; these groups on the one hand require special temporary protection and on the other hand they considerably increase the danger of racemisation and thus yet further complicate the conditions for synthesis.

Surprisingly, it has now been found that it is possible to omit several of these substituted aminoacids, in particular including cystine, from the molecule of somatostatin, or to replace them by simple, optically inactive aminoacids, the physiological activity being retained.

The technical advantage for the synthesis of somatostatin-active substances is already clearly evident from the fact that 13 optically active aminoacids (including 7 with a further protected functional group) are necessary as structural units for the synthesis of somatostatin but, in contrast, it suffices to use at most 7 optically active aminoacids (including only 2 with a further protected functional group) in the case of the compounds according to the invention.

The compounds according to the invention can be prepared by methods known per se. In particular, they are obtained by detaching the protective group or groups from a compound of the formula

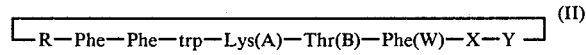 (II)

in which R, W, X, Y and trp are as defined above, A is an ε-amino protective group or hydrogen and B is a hydroxyl protective group or hydrogen, it being posible for only one of the symbols A and B to be hydrogen.

ε-Amino protective groups which can be used are all the amino protective groups customary in peptide chemistry, such as are summarised in the appropriate reference works, for example in Houben-Weyl: Methoden der organischen Chemie (Methods of Organic Chemistry); 4th edition, Volume 15/I, E. Wünsch (Editor): Synthese von Peptiden (Synthesis of Peptides) (Georg Thieme Verlag, Stuttgart; 1974). Preferred groups are those detachable by acidolysis, such as, in particular, the tert.-butoxycarbonyl group and analogous groups, for example the tert.-amyloxycarbonyl, isopropoxycarbonyl, diisopropylmethoxycarbonyl, allyloxycarbonyl, cyclopentyloxycarbonyl, cyclohexyloxycarbonyl, d-isobornyloxycarbonyl and adamantyloxycarbonyl group, and also groups of the aralkyl type, such as benzhydryl and triphenylmethyl (trityl), or certain aralkoxycarbonyl groups of the 2-(p-biphenylyl)-2-propoxycarbonyl type, which have been described in Swiss patent specification No. 509,266.

However, amino protective groups detachable by reduction or under basic conditions can also be used, for example, in particular, the benzyloxycarbonyl group and benzyloxycarbonyl groups which are substituted in the aromatic moiety by halogen atoms, nitro groups, lower alkoxy groups and/or lower alkyl radicals, such as the p-chloro- and p-bromo-benzyloxycarbonyl group, the p-nitrobenzyloxycarbonyl group, the p-methoxybenzyloxycarbonyl group and the p-tolyloxycarbonyl group, or the isonicotinyloxycarbonyl group, and furthermore also acyl groups, such as p-toluenesulphonyl, benzenesulphenyl, o-nitrobenzenesulphenyl and also formyl, trifluoroacetyl or phthaloyl.

A particularly advantageous ε-amino protective group is an ethoxycarbonyl group which in the β-position carries a silyl group substituted by three hydrocarbon radicals, such as a triphenylsilyl, dimethyl-butyl-silyl or, in particular, trimethylsilyl group. A β-trihydrocarbylsilyl)-ethoxycarbonyl group of this type, such as a β-(tri-lower alkylsilyl)-ethoxycarbonyl group, for example in particular the β-(trimethylsilyl)-ethoxycarbonyl group, together with the ε-amino group to be protected forms a corresponding β-trihydrocarbylsilyl-ethoxycarbonylamino group (for example the β-trimethylsilylethoxycarbonylamino group), which is stable to the conditions of acid hydrolysis and of hydrogenolysis but can be detached under very specific, very mild conditions by the action of fluoride ions. In this respect it behaves analogously to the β-silylethyl ester group described further below as a carboxyl protective group. (Particular attention must be paid to this similarity when carrying out the synthesis: except for isolated cases, the use of one of these protective groups precludes the use of the other protective group at the same time.) Further details are given further below in the context of the protection of the carboxyl group by β-silylethyl ester.

Groups which can be used as the hydroxyl protective group are all those customarily used for this purpose in peptide chemistry, cf. the work cited above (Houben-Weyl). Groups detachable by acidolysis are preferred, such as 2-tetrahydropyranyl and very particularly tert.-butyl, and also tert.-butoxycarbonyl. Furthermore, however, hydroxyl protective groups detachable by reduction or under basic conditions can also be used, for example benzyl and benzyloxycarbonyl groups which can be substituted in the aromatic moiety by halogen, nitro and/or lower alkoxy, and the lower alkanoyl radicals, such as acetyl, or aroyl radicals, such as benzoyl.

The protective groups A and B are preferably so chosen that they are detachable under similar conditions; the groups detachable by acidolysis, which have already been mentioned in particular, are especially preferred. Detaching of both protective groups is then advantageously effected in a single operation; however, it is also possible to use groups of different types and to detach each group individually.

The protective groups are detached in the generally known manner; the acid hydrolysis (acidolysis) is carried out, for example, by means of trifluoroacetic acid, hydrochloric acid or hydrogen fluoride and in the case of acid-sensitive protective groups also by means of a lower aliphatic carboxylic acid, such as formic acid and/or acetic acid, in the presence of water and if appropriate of a polyhalogenated lower alkanol or lower alkanone, such as 1,1,1,3,3,3-hexafluoropropan-2-ol or hexafluoroacetone. The groups detachable by reduction, especially those which contain benzyl radicals, are preferably removed by hydrogenolysis, for example by hydrogenation under palladium catalysis. The isonicotinyloxycarbonyl group is preferably detached by reduction with zinc.

Depending on the way in which they are isolated, the end products according to the invention are obtained in the form of bases or in the form of acid addition salts; these can subsequently be converted into one another in a manner known per se.

The abovementioned complexes are also formed by known methods or by methods equivalent to these.

Complexes with inorganic substances such as sparingly soluble metal compounds, for example aluminium or zinc compounds, are preferably prepared in a manner analogous to that known for ACTH, for example by reaction with a soluble salt of the particular metal, for example zinc chloride or zinc sulphate, and precipitation with an alkali metal phosphate and/or alkali metal hydroxide. Complexes with organic compounds such as polyoxygelatine, carboxymethylcellulose, polyvinyl pyrrolidone, polyphloretin phosphate, polyglutamic acid and the like are obtained by mixing these substances with the peptide in aqueous solution. Insoluble compounds with alkali metal polyphosphates can also be prepared in the same way.

The compounds of the formula II characterised above are novel and also constitute a subject of the invention. They are obtained by cyclising a corresponding linear peptide of the formula

H-[II']-C    (III)

in which II' is a radical of the formula II in which the amide bond between any two adjacent aminoacid radicals of the peptide ring is interrupted and C is a free hydroxyl group, a hydroxyl group modified by an activating group or the hydrazino group —NH—NH₂.

Preferred linear peptides of the formula III are those in which at least one of the radicals X and Y in the radical [II'] forms a terminal aminoacid. These preferred starting materials are characterised by the formulae H-X-Y-R-Phe-Phe-trp-Lys(A)-Thr(B)-Phe-C    (IIIa)

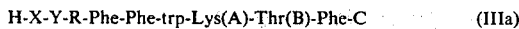

H-Y-R-Phe-Phe-trp-Lys(A)-Thr(B)-Phe-X-C    (IIIb)

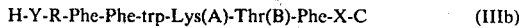

and especially

H-R-Phe-Phe-trp-Lys(A)-Thr(B)-Phe-X-Y-C    (IIIc)

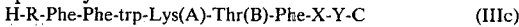

in which A, B, C, trp, R, X and Y are as defined above. Very particularly preferred compounds are those of the formulae IIIa-c in which A is an amino protective group, in particular an amino protective group detachable by acidolysis, B is a hydroxyl protective group, in particular a hydroxyl protective group detachable by acidolysis, and C is a free hydroxyl group.

A functional group represented by the symbol C links with the carbonyl group of the C-terminal aminoacid radical and together with this forms a free carboxyl group, an activated ester group or the carbazoyl group.

An activating group which modifies the hydroxyl groups is in particular an activating group which forms the activated ester of N-hydroxysuccinimide, 1-hydroxybenzotriazole, N,N'-dicyclohexylisourea, 2,4,5-trichlorophenol, 2-nitrophenol, 4-nitrophenol, pentachlorophenol or pentafluorophenol, or also another activating group of this type known from peptide chemistry; cf, Houben-Weyl, Volume 15/II.

The cyclisation, according to the invention, of the linear peptides of the formula III is effected in a manner known per se by means of conventional coupling methods customarily used to form the amide bond, but the peptide starting materials are used in a very low concentration in order to shift the course of the coupling reaction in favour of the intramolecular cyclisation at the expense of the intermolecular polycondensation.

The linear peptides are advantageously used in an approximately $1\times10^{-5}$ molar to about $1\times10^{-3}$ molar concentration, preferably in an approximately $1\times10^{-4}$ molar concentration, which corresponds to a weight-/volume concentration of about 0.01 to 1.0%, preferably 0.1%. The dilution can be adjusted to the appropriate value in the reaction mixture from the start, or can be produced continuously by slow dropwise addition of the starting material and, if desired, of the other regards to the reaction mixture.

The cyclisation is preferably effected by, at an abovementioned initial concentration, (a) treating a starting material of the formula III, in which C is a free hydroxyl group and in which both the ε-amino group of the lysine radical and the hydroxyl group of the threonine radical are protected, with a carbodiimide, if desired in the presence of an active ester-forming component, or (b) reaction a starting material of the formula III, in which C is a hydroxyl group converted to an activated ester and the terminal amino group is in the protonated form and at least the ε-amino group of the lysine radical is protected, with an organic base, or (c) first treating a starting material of the formula III, in which C is the group —NHNH₂ and at least the ε-amino group of the lysine radical is protected, under acid conditions with nitrous acid or a lower alkyl ester thereof and subsequently carrying out the cyclisation, at an abovementioned low concentration, with excess organic base.

The cyclisation is carried out in suitable solvents; examples are dioxan, tetrahydrofuran, acetonitrile, pyridine, dimethylformamide, dimethylacetamide, dimethylsulphoxide, N-methylpyrrolidone, hexamethylphosphoric acid triamide and also chloroform and methylene chloride and mixtures thereof.

In process variant (a), the cyclisation is effected by a carbodiimide, preferably N,N'-dicyclohexylcarbodiimide, which advantageously is used in excess; it is to be assumed that in this reaction the starting material of the formula III containing a free carboxyl group is first converted to an activated ester of dicyclohexylisourea (or of an analogous isourea) and this active ester formed in situ reacts further straightaway. The object of adding an active ester-forming component as an auxiliary reagent is doubtless to effect the formation of an active ester as an intermediate; active ester-forming components which can be used for this purpose are those customary in peptide chemistry, such as, especially, 2,4,5-trichlorophenol, 2- or 4-nitrophenol, pentachlorophenol and pentafluorophenol, but in particular N-hydroxy compounds, particularly advantageous compounds of this type being N-hydroxysuccinimide, N-hydroxypiperidine and in particular 1-hydroxybenzotriazole. The reaction temperature for this variant is in general 0°–70°, and preferably 35°–55°.

In the case of variant (b), in which ready-prepared active esters are used, especially those already indicated as being preferred, the cyclisation takes place spontaneously as the terminal amino group is deprotonised by the organic base. The bases used are preferably quaternary or, in particular, tertiary amines, for example triethylamine or N-ethylmorpholine. The reaction is preferably carried out at 10°–30°, especially at room temperature.

In the case of variant (c), the first phase, i.e. the formation of the acid azide by treatment with nitrous acid or an ester thereof, can advantageously be carried out using the starting materials in a substantially higher concentration than in the subsequent cyclisation. Appropriately, the reaction is carried out with about one equivalent of a lower alkyl nitrite, such as ethyl nitrite, isoamyl nitrite and especially tert.-butyl nitrite, in a hydrochloric acid medium at temperatures of about −30° to about −5°, preferably about −20°; a slight excess of nitrate is permissible. After the necessary dilution, the solution of the azide formed is then rendered alkaline at a temperature of about 0° to about 35° by means of an organic base in excess, for example one of those mentioned above, and by this means is made to undergo spontaneous cyclisation, as in the case of process variant b.

The linear peptides of the formula III and the intermediates used for their synthesis are novel and can advantageously be used to synthesise other somatostatin analogues also, for example those containing longer aminoacid sequences. They, and their methods of preparation, constitute a subject of the present invention. They are obtained by methods known per se, by subjecting the aminoacids required for their build-up, or smaller peptide units, to a condensation reaction with one another in any desired temporal sequence, CONH bonds being formed; functional groups which do not participate in the reaction can be temporarily protected.

Protective groups which can be used for the terminal α-amino and carboxyl groups during the preparation of these starting materials and also of all necessary intermediates are especially the protective groups which are customary in the synthesis of long-chain peptides and can be detached easily and selectively, for example by solvolysis or reduction.

Examples of α-amino protective groups are: di- or tri-aryl-lower alkyl groups, such as diphenylmethyl or triphenylmethyl groups, which are unsubstituted or substituted, for example by halogen, nitro, lower alkyl or lower alkoxy, for example benzhydryl, trityl and di-(p-methoxy)-benzhydryl, or, in particular, groups which are detachable by hydrogenolysis and are derived from carbonic acid, such as benzyloxycarbonyl groups, which can be substituted in the aromatic radical by halogen atoms, nitro groups, lower alkyl groups or lower alkoxy groups, for example benzyloxycarbonyl (i.e. carbobenzoxy), p-bromo- or p-chloro-benzyloxycarbonyl, p-nitrobenzyloxycarbonyl and p-methoxybenzyloxycarbonyl; and also 2-(p-biphenylyl)-2-propoxycarbonyl and similar aryloxycarbonyl groups described in Swiss Patent No. 509,266. Regard must be paid to the fact that it must be possible selectively to detach the α-amino protective group whilst retaining an ε-amino protective group which may be present in the lysine radical. It is, moreover, also advantageous if a carboxyl and hydroxyl protective group, which may be present, also remain unaffected when the α-amino protective group is detached.

Carboxyl groups are protected, for example, by forming a hydrazide or by esterification. Substances suitable for carrying out esterification are, for example, lower, substituted or unsubstituted alkanols, such as methanol, ethanol, cyanomethyl alcohol, 2,2,2-trichloroethanol, benzoylmethyl alcohol or, especially, tert.-butyl alcohol, but also a substituted or unsubstituted benzyl alcohol. A particularly advantageous category of substituted alkanols comprises ethyl alcohols which in the β-position carry a trisubstituted silyl group, such as a triphenylsilyl, dimethyl-butyl-silyl or, in particular, trimethylsilyl group. As described, for example, in Belgian Patent No. 851,576, these alcohols are particularly suitable for protecting carboxyl groups because although the corresponding β-silylethyl esters, for example β-(trimethylsilyl)-ethyl esters have the stability of conventional alkyl esters they can be detached selectively under mild conditions by the action of fluoride ions, all other protective groups being retained.

Substances suitable for forming activated esters, for example in the compounds of the formula III, are, for example, phenols and thiophenols which are unsubstituted or substituted by electron-attracting substituents, such as phenol, thiophenol, thiocresol, p-nitrothiophenol, 2,4,5- and 2,4,6-trichlorophenol, pentachlorophenol, o- and p-nitrophenol, 2,4-dinitrophenol and p-cyanophenol, and also, for example, N-hydroxysuccinimide, N-hydroxyphthalimide and N-hydroxypiperidine.

The hydroxyl group of the threonine radical can be protected by esterification or etherification, as already indicated above; however it can also remain free.

These protective groups can be detached in a known manner. Thus, the benzyloxycarbonyl group can be detached by hydrogenolysis, the N-trityl group can be detached by mineral acids, such as hydrogen halide acids, for example hydrogen fluoride or preferably hydrogen chloride, or an organic acid, such as formic acid, acetic acid, chloroacetic acid or trifluoroacetic acid, in aqueous or absolute trifluoroethanol as the solvent (cf. German Offenlegungsschrift DT No. 2,346,147) or by aqueous acetic acid, the tert.-butoxycarbonyl group can be detached by trifluoroacetic acid or hydrochloric acid and the 2-(p-biphenylyl)-isopropoxycarbonyl group can be detached by aqueous acetic acid or, for example, by a mixture of glacial acetic acid, formic acid (82.8%) and water (7:1:2) or by the process of DT No. 2,346,147.

The β-silylethyl ester groups are preferably detached by reagents which supply fluoride ions, for example fluorides of quaternary organic bases, such as tetraethylammonium fluoride. However, like the customary alkyl esters, they can also be detached by alkaline hydrolysis, for example by means of alkali metal hydroxides, alkali metal carbonates or alkali metal bicarbonates, or converted by hydrazinolysis, for example by means of hydrazine hydrate, to the corresponding carbazoyl groups. Acidolysis is preferably used for detaching tert.-butyl esters and hydrogenolysis for detaching benzyl esters.

The condensation reaction of the aminoacid units and/or peptide units which is to be carried out to prepare the linear peptides of the formula III is effected in a manner known per se, preferably by linking an aminoacid or a peptide which has a protected α-amino group and a terminal carboxyl group which can be activated (=active component) with an aminoacid or a peptide which has a free α-amino group and a free or protected, for example esterified, terminal carboxyl group (=passive component), setting free the terminal amino group in the product formed and reacting this peptide, containing a free α-amino group and a terminal carboxyl group which can be protected, again with a further active component, i.e. an aminoacid or a peptide with an activated terminal carboxyl group and a free α-amino group, and so on. The carboxyl group can be activated, for example, by conversion to an acid azide, acid anhydride, acid imidazolide or acid isoxazolide or an activated ester, such as one of those mentioned above, or by reaction with a carbodiimide, such as N,N'-dicylohexylcarbodiimide, if desired with the addition of N-hydroxysuccinimide or a 1-hydroxybenzotriazole or 4-hydroxybenzo-1,2,3-triazine 3-oxide which is unsubstituted or substituted, for example by halogen, methyl or methoxy (inter alia, cf, DT Nos. 1,917,690, DT 1,937,656 and DT 2,202,613) or with N,N'-carbonyldiimidazole. The most commonly used coupling method is the carbodiimide method, and also the azide method, the activated ester method and the anhydride method, as well as the Merrifield method and the N-carboxyanhydride or N-thiocarboxyanhydride method.

In a particularly preferred preparation of the linear peptides of the formula II the coupling method used is the carbodiimide method with N,N'-dicyclohexylcarbodiimide in the presence of 1-hydroxybenzotriazole. In this case the terminal carboxyl group is protected in the form of the β-(trimethyl-silyl)-ethyl ester and the α-amino group of the active component is protected by the benzyloxycarbonyl group, which after each coupling step is detached by hydrogenolysis. Acylation with a tert.-butoxycarbonyl group is used to protect the ε-amino group of the lysine radical and etherification with a tert.-butyl group is used to protect the hydroxyl group of the threonine radical. These two protective groups can, if desired, finally be detached in one step by acid hydrolysis, for example by means of trifluoroacetic acid, hydrochloric acid or hydrogen fluoride.

Depending on the procedure, the compounds are obtained in the form of bases or of their salts. The bases can be obtained from the salts in a manner known per se. In turn, therapeutically usable acid addition salts can be obtained from the bases by reaction with acids, for example with those which form the abovementioned salts.

Because of the close relationship between the novel compounds in the free form and in the form of their salts, what is stated in this specification in respect of the free compounds or the salts thereof also applies by analogy to the corresponding salts and free compounds.

The invention also relates to those embodiments of the process in which a compound obtainable as an intermediate at any process stage is used as the starting material and the missing process steps are carried out or in which a starting material is formed under the reaction conditions or is used in the form of a derivative thereof, if desired in the form of a salt.

The starting materials used in the process of the present invention are preferably those which result in the compounds described initially as being particularly valuable.

The present invention also relates to pharmaceutical preparations which contain compounds of the formula I or pharmaceutically usable salts thereof. These pharmaceutical preparations can be used, in particular, in the abovementioned indications if they are administered intraperitoneally, such as intravenously, intramuscularly or subcutaneously, or also intranasally. The requisite dose depends on the particular disease to be treated and on its severity and on the period of therapy. The number of single doses and the amount in a single dose and also the administration pattern can best be determined on the basis of an individual examination of the particular patient. The method for determining these factors is well known to those skilled in the art. As a rule, however, a therapeutically effective amount of such a compound in the case of an injection is in the dosage range of about 0.001 to about 0.2 mg/kg of body weight. The range of about 0.0015 to about 0.15 mg/kg of body weight is preferred and the administration is effected by intravenous infusion or subcutaneous injection. Accordingly, pharmaceutical preparations for parenteral administration in the form of a single dose contain, per dose, about 0.08 to about 15 mg of one of the compounds according to the invention, depending on the mode of administration. In addition to the active ingredient, they usually also contain a buffer, for example a phosphate buffer, which is intended to keep the pH between about 3.5 and 7, and also sodium chloride, mannitol or sorbitol in order to render them isotonic. They can be in the freeze-dried or dissolved form and solutions can advantageously contain a preservative having an antibacterial action, for example 0.2–0.3% of methyl 4-hydroxybenzoate or ethyl 4-hydroxybenzoate. If the active ingredient is to be present, in such preparations, in the form of a complex with a longerlasting period of action, this complex can be formed direct by adding the complex-forming component to an injection solution, which is prepared, for example, in accordance with the abovementioned measures. A suitable additive is, for example, 0.1–1.0% by weight of a zinc-II salt (for example the sulphate) in combination with 0.5–5.0% by weight of protamine (for example in the form of the sulphate), based on the total volume of the injection solution; this preparation is in the form of a solution with a pH of 3.5 to about 6.5 or in the form of a suspension with a pH of about 7.5 to 8.0.

A preparation for intranasal administration can be in the form of an aqueous solution or jelly, an oily solution or suspension or a fat-containing ointment. A preparation in the form of an aqueous solution is obtained, for example, by dissolving the active ingredient of the formula I, or a therapeutically usable acid addition salt thereof, in an aqueous buffer solution with a pH of up to 7.2 and adding a substance which produces isotonia. A polymeric adhesive, for example polyvinylpyrrolidone, and/or a preservative are preferably added to the aqueous solution. A single dose is about 0.08 to about 15 mg, preferably 0.25 to 10 mg, and is contained in about 0.05 ml of a solution or 0.05 g of a jelly.

An oily administration form for intranasal administration is obtained, for example, by suspending a peptide of the formula I, or a therapeutically usable acid addition salt thereof, in an oil, if appropriate with the addition of swelling agents, such as aluminium stearate, and/or surface-active agents (surfactants), the HLB value ("hydrophilic-lipophilic balance") of which is less than 10, such as fatty acid monoesters of polyhydric alcohols, for example glycerol monostearate, sorbitan monolaurate, sorbitan monostearate or sorbitan monooleate. A fat-containing ointment is obtained, for example, by suspending the active ingredient according to the invention in a spreadable fat base, if appropriate with the addition of a surfactant with a HLB value of less than 10. An emulsion ointment is obtained by grinding an aqueous solution of the peptide active ingredient in a soft, spreadable fat base with the addition of a surfactant which has a HLB value of less than 10. All of these forms for intranasal administration can also contain preservatives. The single doses are about 0.08 to about 15 mg, preferably 0.25 to 10 mg, contained in about 0.05 to about 0.1 g of the base.

Further suitable preparations for intranasal administration are inhalation or insufflation preparations, such as insufflation capsules, which enable the active ingredient to be unsufflated in the form of a powder with the respiratory air, or aerosols or sprays which can disperse the pharmacological active ingredient in the form of a powder or in the form of drops of a solution or suspension. Preparations having powder-dispersing properties usually contain adjuncts in addition to the active ingredient: insufflation capsules contain, for example, solid carriers, such as lactose; aerosol and spray preparations contain, for example, a liquid propellant gas which has a boiling point below room temperature and also, if desired, further carriers, such as liquid or solid nonionic or anionic surfactants and/or solid diluents. Preparations in which the pharmacological active ingredient is in solution contain, in addition to this ingredient, a suitable propellant, and also, if necessary, an additional solvent and/or a stabiliser. In place of the propellant gas it is also possible to use compressed air, which can be produced as required by means of a suitable compression and pressure let-down device.

The invention also relates to the use of the novel compounds of the formula I and therapeutically usable acid addition salts thereof as pharmacologically active compounds, especially in the indications customary for somatostatin, preferably in the form of pharmaceutical preparations. The daily dose which is administered to a warm-blooded animal weighing about 70 kg is from about 0.1 to about 120 mg.

The following examples illustrate the invention without in any way restricting the scope thereof. Temperatures are given in degrees centigrade; the abbreviations used, for example for the designation of aminoacids, peptides, protective groups and the like, are the customary abbreviations, for example the abbreviations summarised in "Synthese von Peptiden" ("Synthesis of Peptides") (Editor: E. Wünsch), Volume XV of "Methoden der org. Chemie" ("Methods of Organic Chemistry") (Houben-Weyl) (1974; G. Thieme, Stuttgart). In particular, the following abbreviations are used.

Boc—tert.-butoxycarbonyl
Bpoc—2-(p-biphenylyl)-2-propoxycarbonyl
But—tert.-butyl (as ether-forming group)
DCCI—N,N'-dicyclohexylcarbodiimide
Gaba—4-aminobutyric acid radical, —NH—(CH$_2$)$_3$—CO—
OBzl—benzyloxy (as ester-forming group)
ONP—p-nitrophenoxy (as ester-forming group)
ONSu—succinimido-N-oxy
OTmse—2-(trimethylsilyl)-ethoxy (as ester-forming group)
SEOC—2-(trimethylsilyl)-ethoxycarbonyl
Z—benzyloxycarbonyl (carbobenzoxy)
TLC—thin layer chromatography Unless otherwise stated, in TLC silica gel is used as the adsorbent and the following systems are used as the solvents:
System 45: sec.-butanol/3% aqueous ammonia (7:3)
System 52: n-butanol/acetic acid/water (71.5:7.5:21)
System 101: n-butanol/pyridine/acetic acid/water (38:24:8:30)
System 101B: n-butanol/pyridine/25% aqueous ammonia/water (40:24:6:30)
System 112A: n-butanol/pyridine/formic acid/water (42:24:4:20)
System 157: chloroform/methanol/acetic acid/water (70:42:0.5:10)
System 157A: chloroform/methanol/acetic acid/water (90:10:0.5:1)
System 157B: chloroform/methanol/acetic acid/water (85:13:0.5:1.5)
System 157C: chloroform/methanol/acetic acid/water (75:26:0.5:5)

EXAMPLE 1

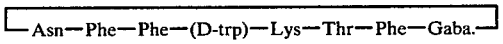

195 mg of protected octapeptide of the formula

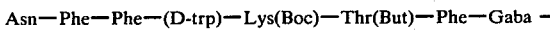

are dissolved at 5° under N$_2$ in 1.5 ml of a mixture of 89% by volume of trifluoroacetic acid, 10% by volume of water and 1% by volume of thioglycollic acid, the solution is immediately warmed to 25° and after 90 minutes at room temperature under N$_2$ the product is precipitated with 15 ml of ether. The resulting crude trifluoroacetate of the end product is dried in vacuo and dissolved in 5 ml of 1 N acetic acid and the solution is filtered through 15 ml of AG ®1X8 (Bio-Rad), acetate form. The eluate is evaporated in vacuo and the residue is subjected to counter-current partitioning in the system n-butanol/acetic acid/water (2,400:600:3,000) over 200 stages. The phases (K=5.9) contained in the elements 168 to 183 are collected, evaporated in vacuo and lyophilised from tert.-butanol/water (1:1).

According to thin layer chromatography in three systems, the resulting title compound is a single compound.

TLC (cellulose, Merck):
System 101: R$_f$0.9
111B: R$_f$0.9
112A: R$_f$0.8

The peptide starting material is obtainable as follows:

Stage 1.1

H-Phe-OTmse hydrochloride

After adding 0.25 g of palladium-on-charcoal (10%), a solution of 2.50 g of Z-Phe-OTmse in 25 ml of methanol is hydrogenated at room temperature and normal pressure for 3 hours, the pH of the reaction mixture being kept at 5.5 by adding a 1N methanolic solution of hydrogen chloride. For working up, the catalyst is filtered off and the filtrate is evaporated in vacuo. The crude product can be used in the next stage without further purification.

Stage 1.2

Z-Thr(But)-Phe-OTmse

A solution of 4.43 ml of isobutyl chloroformate in 20 ml of tetrahydrofuran is added in the course of 3 minutes at −15° to a solution of 10.30 g of Z-Thr(But)OH in 120 ml of anhydrous tetrahydrofuran and 4.20 ml of N-ethylmorpholine. After 10 minutes at −10° to −15°, a solution of 10.05 g of H-Phe-OTmse hydrochloride (see stage 1.1) in 40 ml of tetrahydrofuran and a further portion of 4.20 ml of N-ethylmorpholine are added and the reaction mixture is kept at −15° for 1 hour, at 0° for 1 hour and at room temperature for 1 hour. For working up, the N-ethylmorpholine hydrochloride which has precipitated is filtered off, the filtrate is evaporated in vacuo, the residue is dissolved in ethyl acetate and the solution is washed three times with 1 N citric acid, three times with 1 N sodium bicarbonate and three times with water. The organic phase is dried over sodium sulphate and evaporated in vacuo and the final traces of solvent are removed under a high vacuum. The product is obtained in the form of a viscous yellowish oil, which according to TLC is a single compound. TLC:

[chloroform/methanol (9:1)] $R_f$ 0.83
[ethyl acetate/petroleum ether (7:3)] $R_f$ 0.77

Stage 1.3

H-Thr(But)-Phe-Otmse

After adding 880 mg of palladium-on-charcoal (10%), a solution of 8.84 g of Z-Thr(BUt)-Phe-OTmse (stage 1.2) in 325 ml of methanol is hydrogenated for 5 hours at normal pressure and room temperature. For working up, the catalyst is filtered off and the filtrate is evaporated in vacuo. The oily residue of the product is a single compound according to TLC and is used in stage 1.4 without purification.
TLC: [chloroform/methanol (9:1)] $R_f$ 0.62

Stage 1.3A

Z-(D-trp)-Lys(Boc)-OH

A solution of 21.87 g of DCCI in 100 ml of acetonitrile is added dropwise to a solution of 33.84 g of Z-(D-trp)-OH and 17.42 g of 8-hydroxy-quinoline in 50 ml of acetonitrile at 0°–5° in the course of 45 minutes. After a further 30 minutes at 5°, the dicyclohexylurea which has precipitated is removed by filtering off and washing out with 50 ml of acetonitrile. A solution of 27.09 g of H-Lys(Boc)-OH in 25.9 ml of 4.25 N potassium hydroxide solution and 80 ml of acetonitrile is added to the filtrate and the mixture is left to stand for 15 hours at room temperature. For working up, the reaction mixture is evaporated in vacuo, the residue is taken up in 1 liter of ethyl acetate, the solution is washed with three times 200 ml of 1 N hydrochloric acid at 0° and with three times 200 ml of water and the organic phase is dried over sodium sulphate and evaporated in vacuo. The resulting brown oil is dissolved in 150 ml of chloroform and the solution is added dropwise to 1.5 liters of hexane, with vigorous stirring. The flocculent, tacky precipitate is filtered off, washed with 500 ml of hexane and dried in vacuo. For further purification, the material is dissolved in 150 ml of carbon tetrachloride/ethyl acetate (6:4 parts by volume) and chromatographed on a silica gel column using this solvent mixture.

Suitable fractions which according to thin layer chromatography are a single compound are evaporated in vacuo, by which means the pure product is obtained in the form of a foam-like mass.
TLC: [chloroform/methanol/water (14:6:1)] $R_f$ 0.61

Stage 1.4

Z-(D-trp)-Lys(Boc)-Thr(But)-Phe-OTmse 2.28 g of N-hydroxy-benzotriazole and 3.38 g of DCCI are added, at 5°, to a solution of 7.24 g of crude (87% pure according to titration) H-Thr(But)-Phe-OTmse (stage 1.3) and 8.45 g of Z-(D-trp)-Lys(Boc)-OH (stage 1.3A) in 100 ml of dimethylformamide and the reaction mixture is kept at 5° for 1 hour and at room temperature for a further 15 hours. For working up, the dicyclohexylurea which has precipitated is removed by filtering off and the filtrate is evaporated under a high vacuum. The residue is twice recrystallised from ethyl acetate/petroleum ether and dried in vacuo; melting point 114°–120°.
TLC:

[chloroform/ethyl acetate (1:1)] $R_f$ 0.23;
[toluene/acetone (1:1)] $R_f$ 0.70

Stage 1.5

H-(D-trp)-Lys(Boc)-Thr(But)-Phe-OTmse

After adding 0.50 g of palladium-on-charcoal (10%), a solution of 5.00 g of Z-(D-trp)-Lys(Boc)-Thr(But)-Phe-OTmse (stage 1.4) in 300 ml of methanol is hydrogenated at room temperature and normal pressure for 5 hours. For working up, the catayst is filtered off and the residue which remains after evaporating the filtrate is immediately reacted further in stage 1.6.

Stage 1.5A

Z-Asn-Phe-Phe-OH 2.36 ml of 4 N sodium hydroxide solution and subsequently 5.29 g of Z-Asn-ONP are added to a suspension of 2.95 g of H-Phe-Phe-OH in 30 ml of dimethylformamide and 6 ml of water and the mixture is stirred well for 20 hours at 35°. For working up, 2.36 ml of 4 N hydrochloric acid are added to the reaction solution at 5°, the solution, which has become slightly turbid, is filtered and the filtrate is concentrated to about 15 ml under a high vacuum. The crude product is precipitated in gel-like form by adding 150 ml of water and is filtered off and dried in vacuo over phosphorus pentoxide. This material is then reprecipitated from twice 20 ml of methanol and 50 ml of ether, filtered off and dried in vacuo. According to the racemisation test (total hydrolysis, preparation of derivatives of the aminoacids and separation by gas chromatography), less than 2% by the aminoacids in this product are in the D-configuration.
TLC: [chloroform/methanol/acetic acid/water (70:40:0.5:10)] $R_f$ 0.50

Stage 1.6

Z-Asn-Phe-Phe-(D-trp)-Lys(Boc)-Thr(But)-Phe-OTmse 210 mg of N-hydroxy-benzotriazole and 276 mg of DCCI are added to a solution of 632 mg of Z-Asn-Phe-Phe-OH (stage 1.5A) and 862 mg of H-(D-trp)-Lys(-Boc)-Thr(But)-Phe-OTmse (stage 1.5) and the mixture is left to stand for 15 hours at room temperature. For working up, the dicyclohexylurea which has precipitated is removed by filtering off and the filtrate is evaporated under a high vacuum. The oily residue is ground with 5 ml of methanol and filtered off with suction. The undissolved material, for purification, is again ground with 5 ml of methanol at 50°, filtered off with suction, washed with methanol and dried in vacuo. According to TLC, the product is a single compound.
TLC:
[chloroform/methanol (85:15)] $R_f$ 0.85
[chloroform/methanol/water (14:6:1)] $R_f$ 0.90

Stage 1.7

Z-Asn-Phe-Phe-(D-trp)-Lys(Boc)-Thr(But)-Phe-OH

Z-Asn-Phe-Phe-(D-trp)-Lys(Boc)-Thr(But)-Phe-OTmse (stage 1.6) (940 mg) is dissolved in 23 ml of a freshly prepared anhydrous 0.15 M solution of tetraethylammonium fluoride in dimethylformamide and kept at 25° for 30 minutes. After cooling to 5°, 0.68 ml of 1 N aqueous hydrochloric acid is added to the reaction mixture, with good stirring, and the product is precipitated by adding 70 ml of water. The material filtered off is washed with 5 ml of water, dried in vacuo over phosphorus pentoxide and used direct in stage 1.8.

Stage 1.7A

H-Gaba-OBzl p-toluenesulphonate

A mixture of 30.94 g of 4-aminobutyric acid add 68.48 g of p-toluenesulphonic acid monohydrate in 311 ml of benzyl alcohol and 300 ml of benzene is distilled slowly under normal pressure until a total of 200 ml of a fraction with a boiling point of 70°–90° is collected in the course of 5 hours. The clear reaction solution is concentrated to 150 ml, under a waterpump vacuum and then under a high vacuum at about 60°. The crystal slurry which has precipitated is stirred with 250 ml of ether and the crystals are filtered off and washed with 200 ml of ether. For further purification, this material is stirred with 500 ml of ether at room temperature for one hour, filtered off, washed with ether and dried in vacuo; melting point 106°–107.5°.
TLC: [chloroform/methanol/17% aqueous ammonia/water (50:40:6:4)] $R_f$ 0.39

Stage 1.8

Z-Asn-Phe-Phe-(D-trp)-Lys(Boc)-Thr(But)-Phe-Gaba-OBzl 61 mg of N-hydroxy-benzotriazole and 93 mg of DCCI are added to a mixture of 430 mg of Z-Asn-Phe-Phe-(D-trp-Lys(Boc)-Thr(But)-Phe-OH (stage 1.7) and 82 mg of Gaba benzyl ester (liberated by adding 0.046 ml of N-methyl-morpholine to 152 mg of the corresponding p-toluenesulphonate, see stage 1.7A) and the mixture is left to stand for 20 hours at room temperature. For working up, 10 ml of ice-cold methanol are added to the mixture and the product is filtered off. For further purification, the solid obtained is stirred with 5 ml of warm methanol for 10 minutes, the suspension is cooled to 0° and the pure product is filtered off and dried in vacuo.
TLC: [chloroform/methanol (85:15)] $R_f$ 0.85

Stage 1.9

H-Asn-Phe-Phe-(D-trp)-Lys(Boc)-Thr(But)-Phe-Gaba-OH

After adding 50 mg of palladium-on-charcoal (10%), a solution of 380 mg of Z-Asn-Phe-Phe-(D-trp)-Lys(-Boc)-Thr(But)-Phe-Gaba-OBzl (stage 1.8) in 25 ml of dimethylformamide is hydrogenated for 6 hours at room temperature and normal pressure. For working up, the solution, after filtering off the catalyst, is concentrated to 2 ml under a high vacuum and the product is precipitated with 25 ml of peroxide-free ether, filtered off and dried in vacuo. The crude product is subjected to the next stage 1.10 (cyclisation) without further purification.

Stage 1.10

└─ Asn—Phe—Phe—(D-trp)—Lys(Boc)—Thr(But)—Phe—Gaba ─┘

A solution of 297 mg of crude H-Asn-Phe-Phe-(D-trp)-Lys(Boc)-Thr(But)-Phe-Gaba-OH (stage 1.9), 324 mg of N-hydroxy-benzotriazole and 495 mg of DCCI in 240 ml of dimethylformamide is kept at 50° for 20 hours. For working up, the solvent is evaporated off under a high vacuum at about 30° and the residue is ground with 10 ml of ethyl acetate. The dicyclohexylurea which has precipitated is removed by filtering off and the filtrate is diluted at 50 ml with ethyl acetate, washed with three times 20 ml of 1 N aqueous oxalic acid and then with water until neutral, dried over sodium sulphate and evaporated in vacuo. For purification, the crude product is subjected to counter-current partitioning in the system methanol/water/chloroform/carbon tetrachloride (2,700:675:900:1,575 parts by volume) over 460 stages. The phases (K=0.88) contained in the elements 198 to 240 are combined and evaporated in vacuo. The residue is dissolved in 20 ml of tert.-butanol and lyophilised and this results in a material of the above formula which according to thin layer chromatography is a single compound.
TLC:
[chloroform/methanol (85:15)] $R_f$ 0.18
[chloroform/methanol/water (14:6:1)] $R_f$ 0.77

EXAMPLE 2

└─ Asn—Phe—Phe—(D-trp)—Lys—Thr—Phe—Gaba—Gaba ─┘

In a manner analogous to that described in Example 1, the protected nonapeptide of the formula

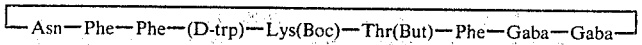

is treated with trifluoroacetic acid and the product is worked up.

By counter-current partitioning (K=5.45) over 200 elements, the desired product is obtained as an amorphous substance which according to thin layer chromatography is a single compound.
TLC: cellulose, Merck;
System 101: $R_f$ 0.90
111B: $R_f$ 0.75
112A: $R_f$ 0.93

The protected nonapeptide used as the starting material is obtainable as follows:

Stage 2.1

Boc-Gaba-OH

The pH of a solution of 41.25 g of H-Gaba-OH in 320 ml of dioxane/water (1:1 parts by volume) is adjusted to 10.0 by means of 20.5 ml of 4 N sodium hydroxide solution and 63.0 g of Boc azide are added. The pH is kept at 10.0 by slowly adding 4 N sodium hydroxide solution (a total of 185 ml) over a period of 24 hours at room temperature. For working up, the reaction solution is washed with three times 250 ml of ether and the pH of the aqueous phase is adjusted to 3.0 by adding 192 g of citric acid, at 5°. The material which has precipitated is taken up in three 400 ml portions of ether and the combined organic phases are washed until neutral, dried over sodium sulphate and evaporated in vacuo. The residue is dissolved in 50 ml of ether and crystallised by adding 100 ml of petroleum ether; melting point 60°–62°.
TLC:
[chloroform/methanol/water (14:6:1)] $R_f$ 0.83
[benzene/acetone (7:3)] $R_f$ 0.21

Stage 2.2

Boc-Gaba-Gaba-OBzl

First 1.39 ml of triethylamine and then, in the course of 1 minute, 1.31 ml of isobutyl chloroformate are added, at −15°, to a solution of 2.03 g of Boc-Gaba-OH (stage 2.1) in 20 ml of anhydrous tetrahydrofuran. After 10 minutes at −10° to −15°, a solution of 3.65 g of H-Gaba-OBzl p-toluenesulphonate (Example 1.7A) and 1.39 ml of triethylamine in 10 ml of dimethylformamide is added at −15° and the reaction mixture is kept at −10° for 1 hour, at 0° for 1 hour and at room temperature for 1 hour. For working up, 150 ml of ethyl acetate are added to the mixture and the resulting mixture is washed three times with 1 N citric acid, three times with 1 N NaHCO₃ and with water. After drying over sodium sulphate, the organic phase is evaporated in vacuo and the residual, slightly yellowish coloured oil is freed from solvent residues under a high vacuum. According to TLC, the product is a single compound.
TLC:
[chloroform/methanol (85:15)] $R_f$ 0.60
[toluene/acetone (7:3)] $R_f$ 0.17

Stage 2.3

H-Gaba-Gaba-OBzl hydrochloride 2.00 g of Boc-Gaba-Gaba-OBzl (stage 2.2) are dissolved in 15 ml of a 2 N solution of hydrogen chloride in ethyl acetate and the solution is left to stand for 1 hour at room temperature. After cooling the reaction mixture to 0°, the product which has precipitated is filtered off, washed with 20 ml of ether and dried in vacuo; melting point 80°–83°.
TLC: [chloroform/methanol/water (14:6:1)] $R_f$ 0.29

Stage 2.4

Z-Asn-Phe-Phe-(D-trp)-Lys(Boc)-Thr(But)-Phe-Gaba-Gaba-OBzl 45 mg of triethylamine, 61 mg of 1-hydroxy-benzotriazole and 93 mg of N,N'-dicyclohexylcarbodiimide are added to a solution of 430 mg of Z-Asn-Phe-Phe-(D-tro)-Lys(Boc)-Thr(But)-Phe-OH (Example 1.7) and 142 mg of H-Gaba-Gaba-OBzl hydrochloride (stage 2.3) in 3 ml of dimethylformamide and the mixture is left to stand for 24 hours at room temperature. 15 ml of water are added to the reaction mixture and the material which has precipitated is filtered off and dried in vacuo over phosphorus pentoxide. For purification, the crude product is ground with 5 ml of hot methanol, filtered off with suction and, after drying in vacuo, precipitated from a solution in 2 ml of dimethylformamide using 10 ml of methanol. The precipitate is filtered off, washed with a little methanol and dried in vacuo, whereupon a product results which is a single compound according to thin layer chromatography.
TLC: [chloroform/methanol (85:15)] $R_f$ 0.80

Stage 2.5

H-Asn-Phe-Phe-(D-trp)-Lys(Boc)-Thr(But)-Phe-Gaba-Gaba-OH

This compound is obtained in a manner analogous to that in Example 1.9, by hydrogenation of Z-Asn-Phe-Phe-(D-trp)-Lys(Boc)-Thr(But)-Phe-Gaba-Gaba-OBzl (stage 2.4), and is further processed in stage 2.6 without purification.

Stage 2.6

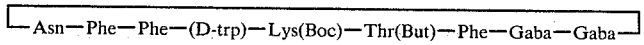

This compound is obtained in a manner analogous to that in Example 1.10, by cyclising H-Asn-Phe-Phe-(D-trp)-Lys(Boc)-Thr(But)-Phe-Gaba-Gaba-OH (stage 2.5) by means of DCCI and 1-hydroxybenzotriazole. The crude product is purified by counter-current partitioning (K=1.1).
TLC:
[chloroform/methanol (85:15)] $R_f$ 0.06
[chloroform/methanol/water (14:6:1)] $R_f$ 0.69.

EXAMPLE 3

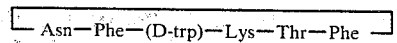

In a manner analogous to that described in Example 1, the protected peptide of the formula

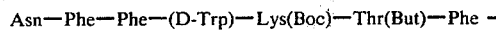
Asn—Phe—Phe—(D-Trp)—Lys(Boc)—Thr(But)—Phe is treated with trifluoroacetic acid and the reaction product is further processed. The desired product is obtained as an amorphous substance by counter-current partitioning (K=3.4) over 220 stages.
TLC:
System 101 $R_f$ 0.60
111B $R_f$ 0.37
112A $R_f$ 0.50

The protected peptide of the formula indicated above which is used as the starting material is obtainable as follows: 1.10 g of Z-Asn-Phe-(D-Trp)-Lys(Boc)-Thr(But)-Phe-OH (Example 1.7) are hydrogenated in 30 ml of dimethylformamide with the addition of 100 mg of Pd-on-charcoal (10%) until complete detaching of the Z group has been effected (about 4 hours, TLC monitoring). After filtering off the catalyst, the filtrate is concentrated to 15 ml under a high vacuum and the resulting solution of the peptide of the formula H-Asn-Phe-Phe-(D-Trp)-Lys(Boc)-Thr(But)-Phe-OH is cyclised direct in a manner analogous to that in Example 1.10, by means of DCCI and N-hydroxybenzotriazole. The crude product is purified by counter-current partitioning (K=0.71) and the desired protected cyclopeptide of the formula

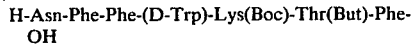
Asn—Phe—Phe—(D-Trp)—Lys(Boc)—Thr(But)—Phe results.
TLC: [chloroform/methanol/water (14:6:1)] $R_f$ 0.83

EXAMPLE 4

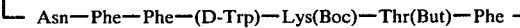
Asn—Phe—Phe—(D-Trp)—Lys—Thr—Phe—NH(CH$_2$)$_4$CO

In a manner analogous to that described in Example 1, the protected peptide of the formula

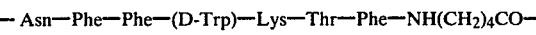
Asn—Phe—Phe—(D-Trp)—Lys(Boc)—Thr(But)—Phe—NH—(CH$_2$)$_4$—CO is treated with trifluoroacetic acid and the reaction product is worked up. The desired product is obtained as an amorphous substance by counter-current partitioning (K=3.31) over 220 stages.
TLC:
System 101 $R_f$ 0.29
111B $R_f$ 0.34
112A $R_f$ 0.47

The protected peptide used as the starting material is obtained as follows:

Stage 4.1

H-Asn-Phe-Phe-(D-Trp)-Lys(Boc)-Thr(But)-Phe-OTmse 942 mg of Z-Asn-Phe-Phe-(D-Trp)-Lys(Boc)-Thr(But)-Phe-OTmse (Example 1.6) are hydrogenated in 50 ml of dimethylformamide with the addition of 100 mg of Pd-oncharcoal (10%) until complete detaching of the Z group has been effected (about 2 hours, TLC monitoring). After filtering off the catalyst, the filtrate is concentrated to 4 ml under a high vacuum and employed direct in the next stage.

Stage 4.2

Z-NH-(CH$_2$)$_4$CO-Asn-Phe-Phe-(D-Trp)-Lys(Boc)-Thr(But)-Phe-OTmse

A solution of 182 mg of DCCI in 1 ml of dimethylformamide is added, at 0°-5°, to a solution of 188 mg of 5-benzyloxycarbonylaminopentanoic acid, 847 mg of the crude heptapeptide from the preceding stage 4.1 and 101 mg of hydroxybenzotriazole in 4 ml of dimethylformamide. After 15 minutes at 0°-5°, the mixture is kept at room temperature for a further 18 hours and the dicyclohexylurea which has precipitated is then filtered off. The filtrate is concentrated to 3 ml under a high vacuum and the crude product is precipitated by adding 60 ml of water. After filtering off and drying, the precipitate is twice stirred with, in each case, 20 ml of methanol at 40° and filtered off, in order to purify it.
TLC:
[chloroform/methanol (85:15)] $R_f$ 0.61
[chloroform/methanol/water (14:6:1)] $R_f$ 0.89

Stage 4.3

Z-NH-(CH$_2$)$_4$CO-Asn-Phe-Phe-(D-Trp)-Lys(Boc)-Thr(But)-Phe-OH 760 mg of Z-NH(CH$_2$)$_4$CO-Asn-Phe-Phe-(D-Trp)-Lys(Boc)-Thr(But)-Phe-OTmse (stage 4.2) are dissolved in 17.1 ml of a freshly prepared anhydrous 0.15M solution of tetraethylammonium fluoride in dimethylformamide and the solution is kept at room temperature for 40 minutes. After cooling to 0°-5°, 0.51 ml of 1 N aqueous hydrochloric acid is added to the reaction mixture, with good stirring, and the product is precipitated by adding 80 ml of water.
TLC:
[chloroform/methanol (85:15)] $R_f$ 0.13
[chloroform/methanol/water (14:6:1)] $R_f$ 0.65

Stage 4.4

NH$_2$(CH$_2$)$_4$CO-Asn-Phe-Phe-(D-Trp)-Lys(Boc)-Thr(But)-Phe-OH 696 mg of Z-NH(CH$_2$)$_4$CO-Asn-Phe-Phe-(D-Trp)-Lys(Boc)Thr(But)-Phe-OH (stage 4.3) are hydrogenated in 70 ml of dimethylformamide with the addition of 80 mg of Pd-on-charcoal (10%) until complete detaching of the Z group has been effected (about 2 hours, TLC monitoring). After filtering off the catalyst, the filtrate is concentrated to about 3 ml under a high vacuum and the product is precipitated with 50 ml of peroxide-free ether.
TLC:
[chloroform/methanol/water (14:6:1)] $R_f$ 0.46

Stage 4.5

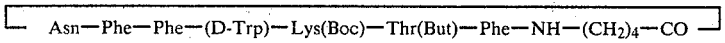
⌞ Asn—Phe—Phe—(D-Trp)—Lys(Boc)—Thr(But)—Phe—NH—(CH₂)₄—CO ⌟

Cyclisation of the linear octapeptide of the formula NH₂(CH₂)₄CO-Asn-Phe-Phe-(D-Trp)-Lys(Boc)-Thr(But)-Phe-OH (stage 4.4) analogously to the procedure described in Example 1.10, by means of DCCI and N-hydroxybenzotriazole, results in the desired cyclic peptide. The crude product is purified by counter-current partitioning (K=0.66).
TLC:
[chloroform/methanol (85:15)] $R_f$ 0.50
[chloroform/methanol/water (14:6:1)] $R_f$ 0.77

EXAMPLE 5

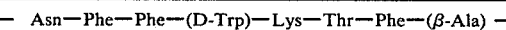
⌞ Asn—Phe—Phe—(D-Trp)—Lys—Thr—Phe—(β-Ala) ⌟

In a manner analogous to that described in Example 1, the protected peptide of the formula

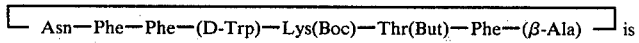
⌞ Asn—Phe—Phe—(D-Trp)—Lys(Boc)—Thr(But)—Phe—(β-Ala) ⌟ is is treated with trifluoroacetic acid and the reaction product is worked up. The desired product is obtained as an amorphous substance by counter-current partitioning (K=5.0) over 170 stages.
TLC:
System 101 $R_f$ 0.53
111B $R_f$ 0.32
112A $R_f$ 0.39

The protected cyclopeptide used as the starting material is obtained as follows:

Stage 5.1

H-(β-Ala)-OBzl p-toluenesulphonate

The desred ester is obtained in the form of the p-toluenesulphonate with a melting point of 94.5°–101° by esterification of β-alanine with benzyl alcohol in the presence of p-toluenesulphonic acid, in a manner analogous to that in Example 1.7A.
TLC:
[chloroform/methanol/water (14:6:1)] $R_f$ 0.38

Stage 5.2

Z-Asn-Phe-Phe-(D-Trp)-Lys(Boc)-Thr(But)-Phe-(β-Ala)-OBzl

In a manner analogous to that in Example 1.8, 1.09 g of Z-Asn-Phe-Phe-(D-Trp)-Lys(Boc)-Thr(But)-Phe-OH (Example 1.7) are reacted with 0.33 g of H-(β-Ala)-OBzl p-toluenesulphonate by means of DCCI in the presence of N-methylmorpholine and N-hydroxybenzotriazole and the reaction product is worked up.
TLC:

[chloroform/methanol (85:15)] $R_f$ 0.69
[chloroform/methanol/water (14:6:1)] $R_f$ 0.89

Stage 5.3

H-Asn-Phe-Phe-(D-Trp)-Lys(Boc)-Thr(But)-Phe-(β-Ala)-OH

In a manner analogous to that in Example 1.9, the benzyl ester H-Asn-Phe-Phe-(D-Trp)-Lys(Boc)-Thr(But)-Phe-(β-Ala)-OBzl (stage 5.2) is converted to the corresponding free acid by hydrogenation.
TLC:
[chloroform/methanol/water (14:6:1)] $R_f$ 0.52

Stage 5.4

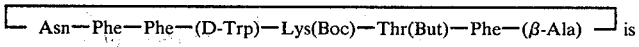
⌞ Asn—Phe—Phe—(D-Trp)—Lys(Boc)—Thr(But)—Phe—(β-Ala) ⌟ is

The free acid H-Asn-Phe-Phe-(D-Trp)-Lys(Boc)-Thr(But)-Phe-(β-Ala)-OH is cyclised by means of DCCI and N-hydroxybenzotriazole by a procedure analogous to that described in Example 1.10. The crude product is purified by counter-current partitioning (K=0.71).
TLC:
[chloroform/methanol (85:15)] $R_f$ 0.65
[chloroform/methanol/water (14:6:1)] $R_f$ 0.80

EXAMPLE 6

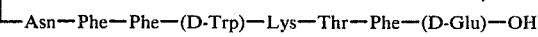
⌞Asn—Phe—Phe—(D-Trp)—Lys—Thr—Phe—(D-Glu)—OH

In a manner analogous to that described in Example 1, the protected peptide of the formula

⌞Asn—Phe—Phe—(D-Trp)—Lys(Boc)—Thr(But)—Phe—(D-Glu)—OBut is treated with trifluoroacetic acid and the reaction product is worked up. The desired product is obtained as an amorphous substance by counter-current partitioning (K=4.26) over 300 stages.
TLC:
101 $R_f$ 0.53
111B $R_f$ 0.40
112A $R_f$ 0.31

(The symbol —Glu—OH represents the radical of the formula

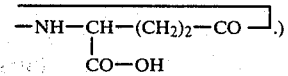
—NH—CH—(CH₂)₂—CO ⌟ .)
  |
  CO—OH

The protected peptide used as the starting material is obtained as follows:

Stage 6.1

H-[D-Glu(OBzl)]-OBut hydrochloride

A mixture of 5.00 g of H-[D-Glu(OBzl)]-OH and 40 ml of liquid isobutene is stirred with 4 ml of concentrated sulphuric acid in 40 ml of dioxan in a closed vessel at room temperature until a clear solution forms and is then left to stand for a further 4 hours at room temperature. For working up, the reaction mixture, which has been cooled to −20°, is poured into an ice-cold mixture of 300 ml of ether and 203 ml of 1 N sodium hydroxide. The ether phase is washed with three times 50 ml of water. After post-extraction of the aqueous phase with a further 300 ml of ether, the combined organic phases are dried over sodium sulphate and concentrated to 10 ml in vacuo, and 30 ml of a 0.7N solution of hydrogen chloride in methanol are added at 0°, with good stirring. The resulting solution is evaporated in vacuo and the residue is ground with 20 ml of petroleum ether until crystallisation takes place. The product of the formula

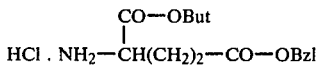

which is filtered off, is purified by chromatography on a column of silica gel (170 g) by means of chloroform/methanol (85:15); melting point 107°–108° (decomposition); $[\alpha]_D^{25}: -15° \pm 1°$ (ethanol, 2%).
TLC [chloroform/methanol (85:15)] $R_f$ 0.60

Stage 6.2

Z-Asn-Phe-Phe-(D-Trp)-Lys(Boc)-Thr(But)-Phe-D-Glu(OBzl)-OBut

A solution of 0.21 g of DCCI in 2 ml of dimethylformamide is added, at 0°–5°, to a solution of 1.09 g of Z-Asn-Phe-Phe-(D-Trp)-Lys(Boc)-Thr(But)-Phe-OH (Example 1.7), 0.31 g of HCl.[D-Glu(OBzl)]-OBut (stage 6.1), 0.13 g of N-hydroxybenzotriazole and 95 mg of N-methylmorpholine in 8 ml of dimethylformamide and after 30 minutes at 0°–5° the mixture is kept at room temperature for a further 15 hours. The dicyclohexylurea which has precipitated is filtered off and the filtrate is evaporated under a high vacuum. The residue is ground with 30 ml of water, filtered off, dried and, for purification, twice more stirred with, in each case, 10 ml of methanol and filtered off.
TLC:
[chloroform/methanol (85:15)] $R_f$ 0.85
[chloroform/methanol/water (14:6:1)] $R_f$ 0.91

Stage 6.3

H-Asn-Phe-Phe-(D-Trp)-Lys(Boc)-Thr(But)-Phe-[D-Glu]-OBut

In a manner analogous to that in Example 1.9, the compound of the formula H-Asn-Phe-Phe-(D-Trp)-Lys(Boc)-Thr(But)-Phe-[D-Glu(OBzl)]-OBut (Stage 6.2) is hydrogenated to the desired product.
TLC:
[chloroform/methanol (85:15)] $R_f$ 0.13
[chloroform/methanol/water (14:6:1)] $R_f$ 0.65

Stage 6.4

In a manner analogous to that described in Example 1.10, the acid of the formula H-Asn-Phe-Phe-(D-Trp)-Lys(Boc)-Thr(But)-Phe-[D-Glu]-OBut is cyclised by means of DCCI and N-hydroxybenzotriazole. The crude product is purified by counter-current partitioning (K=0.52).
TLC:
[chloroform/methanol (85:15)] $R_f$ 0.54
[chloroform/methanol/water (14:6:1)] $R_f$ 0.83

EXAMPLE 7

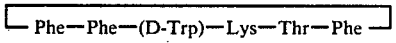

235 mg of protected hexapeptide of the formula

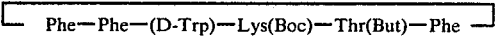

are freed from the protective groups with trifluoroacetic acid, analogously to Example 1, and purified, as the acetate, by counter-current partitioning in the same system as in Example 1. The pure substance is isolated at K=5.4.
TLC (silica gel, Merck):
System 45:$R_f$ 0.2
52:$R_f$ 0.35
157:$R_f$ 0.5
The starting material is obtained as follows:

State 7.1

Z-Phe-Phe-(D-Trp)-Lys(Boc)-Thr(But)-Phe-OTmse 0.62 g of N-hydroxy-benzotriazole and 0.98 g of DCCI are added, at 0°, to a solution of 2.84 g of H-(D-Trp)-Lys(Boc)-Thr(But)-Phe-OTmse (Example 1.5) and 1.52 g of Z-Phe-Phe-OH in 12 ml of dimethylformamide and the mixture is left to stand for 16 hours at 0°. After filtering off the dicyclohexylurea, the product is precipitated by adding the filtrate dropwise to dilute sodium bicarbonate solution. The product is recrystallised from aqueous methanol.
TLC (silica gel, Merck): System 157A, $R_f$ 0.6.

Stage 7.2

Z-Phe-Phe-(D-Trp)-Lys(Boc)-Thr(But)-Phe-OH 6.1 ml of a 1.12 M solution of tetrabutylammonium fluoride in dimethylsulphoxide are added to a solution of 2.86 g of Z-Phe-Phe-(D-Trp)-Lys-(Boc)-Thr(But)-Phe-OTmse in 13.5 ml of dimethylformamide at 30° and the mixture is left to stand for 5 minutes at this temperature. The product is precipitated by adding the reaction mixture dropwise to ice-cold dilute hydrochloric acid and is purified by reprecipitation from acrylonitrile solution with dilute hydrochloric acid.
TLC: System 157A $R_f$ 0.35

Stage 7.3

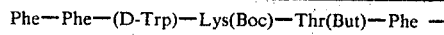

A solution of 870 mg of Z-Phe-Phe-(D-Trp)-Lys(Boc)-Thr(But)-Phe-OH in 20 ml of dimethylformamide is hydrogenated in the preence of 90 mg of palladium-on-charcoal (10%) for 2 hours at room temperature. After filtering off the catalyst, the filtrate is concentrated to a few ml under a high vacuum, 790 ml of dimethylformamide, 1.2 g of N-hydroxybenzotriazole and 1.6 g of DCCI are added and the mixture is left to stand for 15 hours at 50°. After adding 2 ml of a 5 M solution of oxalic acid in dimethylformamide, the mixture is concentrated to about 10 ml under a high vacuum, the dicyclohexylurea is filtered off with suction and the product is precipitated by adding the filtrate dropwise to dilute sodium bicarbonate solution. The pure product is eluted by chromatography on silica gel using chloroform with the addition of 3-5% of methanol.
TLC: System 157A $R_f$ 0.5

EXAMPLE 8

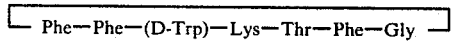

450 mg of

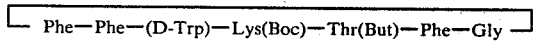

are treated in the manner described in Example 1 with trifluoroacetic acid. The crude product is converted to the acetate using an ion exchanger and this acetate is purified by counter-current partitioning in the system n-butanol/acetic acid/water/toluene (4:1:5:4) over 420 stages. The pure substance (K=1.5) is isolated in the customary manner.
TLC (silica gel, Merck): System 157C $R_f$ 0.25

The starting material is obtained as follows:

Stage 8.1

Z-Phe-Phe-(D-Trp)-Lys(Boc)-Thr(But)-Phe-Gly-OBzl 0.095 ml of N-methylmorpholine and 200 mg of DCCI are added, at 0°, to a solution of 800 mg of Z-Phe-Phe-(D-Trp)-Lys(Boc)-Thr(But)-Phe-0H (Example 7.2), 290 mg of H-Gly-OBzl p-toluenesulphonate and 130 mg of N-hydroxybenzotriazole in 4 ml of dimethylformamide and the mixture is left to stand for 16 hours at 0°. After filtering off the dicyclohexylurea, the product is precipitated by adding the filtrate dropwise to dilute sodium bicarbonate solution. The crude product is purified by recrystallisation from methanol/water (9:1) and acetonitrile/water (1:1).
TLC:
[chloroform/methanol (95:5)]:$R_f$ 0.55
System 157A:$R_f$ 0.75

Stage 8.2

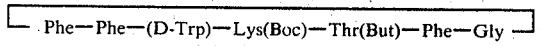

A solution of 780 mg of Z-Phe-Phe-(D-Trp)-Lys(Boc)-Thr(But)-Phe-Gly-OBzl (stage 8.1) in 15 ml of dimethylformamide is hydrogenated in the presence of 80 mg of palladium-on-charcoal (10%) for 6 hours. After filtering off the catalyst, the filtrte is concentrated greatly, 115 ml of dimethylformamide, 910 mg of N-hydroxybenzotriazole and 1.22 g of DCCI are added and the mixture is left to stand for 20 hours at 50°. Working up is carried out as described in Example 7.3. In order to purify the crude product, a counter-current partitioning over 460 stages is carried out the same system as described in Example 1.10. (K=0.4)
TLC: System 157A:$R_f$ 0.4

EXAMPLE 9

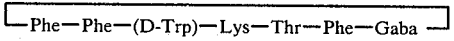

260 mg of

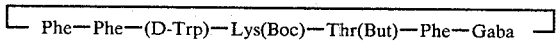

are treated with trifluoroacetic acid, analogously to Example 1. By means of an ion exchanger, the product is converted to the acetate, which is purified by counter-current partitioning over 300 stages in the system sec.-butanol/water/acetic acid (100:100:1). The pure substance (K=1.5) is isolated in the customary manner.
TLC: (silica gel, Merck): System 157 $R_f$ 0.5

The starting material is obtained as follows:

Stage 9.1

Z-Phe-Phe-(D-Trp)-Lys(Boc)-Thr(But)-Phe-Gaba-OBzl 0.05 ml of N-methylmorpholine and 100 mg of DCCI are added, at 0°, to a solution of 420 mg of Z-Phe-Phe-(D-Trp)-Lys(Boc)-Thr(But)-Phe-OH (Example 7.2), 165 mg of H-Gaba-OBzl p-toluenesulphonate and 70 mg of N-hydroxybenzotriazole in 2 ml of dimethylformamide and the mixture is left to stand for 20 hours at 0°. After filtering off the dicyclohexylurea, the product is precipitated by adding the filtrate dropwise to sodium bicarbonate solution.
TLC: System 157A: $R_f$ 0.65

Stage 9.2

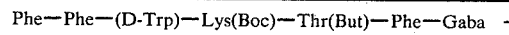

A solution of 500 mg of Z-Phe-Phe-(D-Trp)-Lys(Boc)-Thr(But)-Phe-Gaba-OBzl in 20 ml of dimethylformamide is hydrogenated in the presence of 50 mg of palladium-on-charcoal (10%) for 2 hours. After filtering off the catalyst, the filtrate is concentrated greatly under a high vacuum, 370 ml of dimethylformamide, 560 mg of N-hydroxybenzotriazole and 760 mg of DCCI are added to the residue and the mixture is left to stand for 18 hours at 50°. Working up and purification of the product are carried out analogously to Example 8.2; K=0.3.
TLC: System 157A:$R_f$ 0.45

EXAMPLE 10

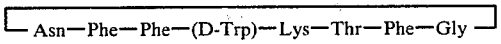

In the manner described in Example 1, 600 mg of

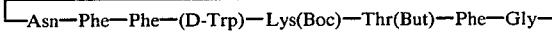

are treated with trifluoroacetic acid and the product is worked up and purified; K=3.5.
TLC: System 157C: $R_f 0.15$
The starting material is obtained as follows:

Stage 10.1

Z-Asn-Phe-Phe-(D-Trp)-Lys(Boc)-Thr(But)-Phe-Gly-OBzl 0.025 ml of N-methylmorpholine and 53 mg of DCCI are added, at 0°, to a solution of 230 mg of Z-Asn-Phe-(D-Trp)-Lys(Boc)-Thr(But)-Phe-OH (Example 1.7), 77 mg of H-Gly-OBzl p-toluenesulphonate and 35 mg of N-hydroxybenzotriazole in 1 ml of dimethylformamide. After 16 hours, the reaction product is worked up analogously to Example 7.1 and recrystallised from acetonitrile/water (4:1).
TLC: System 157A: $R_f 0.65$

Stage 10.2

A solution of 200 mg of Z-Asn-Phe-Phe-(D-Trp)-Lys(Boc)-Thr(But)-Phe-Gly-OBzl (stage 10.1) in 15 ml of dimethylformamide is hydrogenated in the presence of 50 mg of palladium-on-charcoal (10%). After filtering off the catalyst, the filtrate is concentrated under a high vacuum, 140 ml of dimethylformamide, 215 mg of N-hydroxybenzotriazole and 290 mg of DCCI are added to the residue and the mixture is left to stand for 20 hours at 50°. Working up and purification are carried out as in Example 8.2; K=0.8.
TLC: System 157B: $R_f 0.45$

EXAMPLE 11

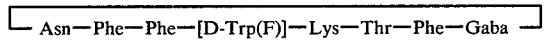

As described in Example 1, 340 mg of

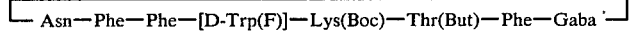

are treated with trifluoroacetic acid and the product is converted to the acetate by means of an ion exchanger and purified by counter-current partitioning in the system tert.-butanol/toluene/methanol/buffer (0.05 M ammonium acetate + 0.05 M acetic acid) (7:7:3:10) over 500 stages (K=0.14).
(The symbol [D-Trp(F)] denotes 5-fluoro-D-tryptophan.)
TLC: System 157: $R_f 0.36$
The starting material is obtained as follows:

Stage 11.1

Z-[D-Trp(F)]-OH 1.4 ml of benzyl chloroformate and 10.5 ml of 1 N sodium hydroxide solution are added at the same time to a solution of 2 g of 5-fluoro-DL-tryptophan in 9 ml of 1 N sodium hydroxide solution, with ice-cooling and vigorous stirring. After a further 2 hours, 50 ml of ethyl acetate are added, the pH of the two-phase mixture is adjusted to 1 with hydrochloric acid and the organic phase is separated off, washed with water, dried over sodium sulphate and evaporated. The residue is dissolved in 9.5 ml of water and 5 ml of 2 N sodium hydroxide solution and after adding 1.5 ml of aniline, 100 mg of L-cysteine hydrochloride and 34 ml of 0.2 M citrate buffer (pH 5), the starting material partially precipitates out again; the pH of the suspension is brought to 6.3 with 2 N hydrochloric acid. 260 mg of papain are suspended in 2 ml of water at 40°, the insoluble matter is centrifuged down and 1.9 ml of the supernatant solution are added to the above suspension and this is stirred for 20 hours at 40°. The pH of the mixture is brought to 8 with 2 N sodium hydroxide solution, with ice-cooling, the insoluble Z-[L-Trp(F)] anilide is filtered off, the pH of the filtrate is adjusted to 5.3 with 5 N hydrochloric acid and cysteine hydrochloride and papain are added, as above. After a further 20 hours, the anilide formed is again filtered off and the filtrate is again treated in the same way as above over a period of 3 days, by which means only traces of the anilide are still formed. The filtrate is covered with a layer of ethyl acetate and acidified to pH 1—2; the organic layer is washed with water, dried over sodium sulphate and evaporated. The residue is recrystallised from diisopropyl ether/hexane.
TLC: System 157B: $R_f 0.3$

Stage 11.2

Z-[D-Trp(F)]-Lys(Boc)-OH 1.15 g of Z-[D-Trp(F)]-OH are converted by the procedure described in Example 1.3A into the dipeptide named in the title.
TLC: System 157B: $R_f 0.33$

Stage 11.3

Z-[D-Trp(F)]-Lys(Boc)-Thr(But)-Phe-OTmse 170 mg of DCCI are added, at 0°, to a solution of 380 mg of z-[D-Trp(F)]-Lys(Boc)-OH, 300 mg of H-Thr(But)-Phe-OTmse (Example 1.3) and 110 mg of N-hydroxybenzotriazole in 2.5 ml of dimethylformamide. After 15 hours, the reaction mixture is worked up analogously to Example 7.1 and the product is purified by recrystallisation from ethyl acetate/petroleum ether.
TLC: System 157A: $R_f 0.76$

Stage 11.4

Z-Asn-Phe-Phe-[D-Trp(F)]-Lys(Boc)-Thr(But)-Phe-OTmse

A solution of 490 mg of Z-[D-Trp(F)]-Lys(Boc)-Thr(But)-Phe-OTmse in 15 ml of methanol/water (9:1) is hydrogenated in the presence of 50 mg of palladium-on-charcoal (10%), the pH being kept continuously at 5 by adding 0.2 N hydrochloric acid in the abovementioned solvent at the same time. The reaction mixture is filtered and the filtrate is concentrated and three times dehydrated by evaporating with dimethylformamide. 305 mg of Z-Asn-Phe-Phe-OH, 83 mg of N-hydroxybenzotriazole, 0.06 ml of N-methylmorpholine and 1.2 ml of dimethylformamide are added to the residual solution (1.2 g). 130 mg of DCCI are added at −5° and the mixture is left to stand for 16 hours at this temperature. After working up analogously to Example 7.1, the product is recrystallised from acetonitrile/water.
TLC: System 157A: $R_f 0.6$

Stage 11.5

Z-Asn-Phe-Phe-[D-Trp(F)]-Lys(Boc)-Thr(But)-Phe-OH 3.8 ml of a 0.34 M solution of tetraethylammonium fluoride in dimethylsulphoxide are added, at 30°, to a solution of 600 mg of Z-Asn-Phe-Phe-[D-Trp(F)]-Lys(Boc)-Thr(But)-Phe-OTmse in 4.2 ml of dimethylformamide and the mixture is left to stand for 30 minutes at 30°. The solution is added dropwise to 50 ml of water and 0.65 ml of 2 N hydrochloric acid, with ice-cooling, and the precipitate is filtered off. The product is purified by recrystallisation from acetonitrile/water.
TLC: System 157A: $R_f 0.35$

Stage 11.6

Z-Asn-Phe-Phe-[D-Trp(F)]-Lys(Boc)-Thr(But)-Phe-Gaba-OBzl 0.05 ml of N-methylmorpholine and 100 mg of DCCI are added, at −5°, to a solution of 470 mg of Z-Asn-Phe-Phe-[D-Trp(F)]-Lys(Boc)-Thr(But)-Phe-OH, 165 mg of H-Gaba-OBzl p-toluenesulphonate (Example 1.7A) and 66 mg of N-hydroxybenzotriazole in 2 ml of dimethylformamide. After 16 hours at this temperature, the reaction mixture is worked up analogously to Example 7.1. Except for traces of dicyclohexylurea, the product is obtained in the pure form.
TLC: System 157A: $R_f 0.55$

Stage 11.7

⌊— Asn—Phe—Phe—[D-Trp(F)]—Lys(Boc)—Thr(But)—Phe—Gaba —⌋

A solution of 520 mg of Z-Asn-Phe-Phe-[D-Trp(F)]-Lys(Boc)-Thr(But)-Phe-Gaba-OBzl in 20 ml of dimethylformamide is hydrogenated in the presence of 50 mf of palladium-on-charcoal (10%) for 2 hours. After filtering off the catalyst, the filtrate is concentrated under a high vacuum and 350 ml of dimethylformamide, 540 mg of N-hydroxybenzotriazole and 720 mg of DCCI are added. After 20 hours at 50°, the product is worked up and purified analogously to Example 8.2; K=1.1.
TLC: System 157A: $R_f 0.35$

EXAMPLE 12

⌊—Asn—Phe—Phe—[D-Trp(NO₂)]—Lys—Thr—Phe—Gaba—⌋

In a manner analogous to that described in Example 1, the protected peptide of the formula ⌊— Asn—Phe—Phe—[D-Trp(NO₂)]—Lys(Boc)—Thr(But)—Phe—Gaba —⌋ is treated with trifluoroacetic acid and the reaction product is worked up. By counter-current partitioning over 220 stages (K=4.5), the desired product is obtained as an amorphous substance which according to thin layer chromatography is a single compound.
TLC:
System 101:$R_f 0.58$
111B:$R_f 0.40$
112A:$R_f 0.45$
(The symbol [D-Trp(NO₂)] denotes 6-nitro-D-tryptophan.)

The starting material is obtained as follows:

Stage 12.1

Z-Gaba-OTmse

A solution of 5.93 g of Z-Gaba-OH and 3.84 g of trimethylsilyl-ethanol in 10 ml of acetonitrile and 6 ml of pyridine is cooled to 5° and 5.70 g of DCCI are added, with stirring. After 1 hour at 5°, the reaction mixture is kept at room temperature for a further 15 hours. The dicyclohexylurea which has precipitated is filtered off and washed with ethyl acetate and the filtrate is evaporated. The residue is chromatographed on a column of silica gel (350 g), a mixture of carbon tetrachloride and ethyl acetate (6:4) being used as the eluent. The fractions containing the product are combined and evaporated. The resulting colourless oil is dried under a high vacuum.
TLC:
[chloroform/methanol (85:15)] $R_f 0.69$
[toluene/acetone (7:3)] $R_f 0.59$

Stage 12.2

H-Gaba-OTmse

After adding 0.5 g of palladium-on-charcoal (10%), hydrogen is passed through a solution of 4.70 g of Z-Gaba-OTmse (stage 12.1) in 50 ml of isopropanol until no further starting material is detectable by thin layer chromatography [chloroform/methanol (85:15)]. The catalyst is filtered off and the filtrate is evaporated in vacuo. The resulting oily crude product is used direct for the next stage.

Stage 12.3

Z-Phe-Gaba-OTmse

A solution of 3.75 g of dicyclohexylcarbodiimide in 5 ml of methylene chloride is added, at 0°–5°, to a solution of 4.60 g of Z-Phe-OH and 2.83 g of H-Gaba-OTmse (stage 12.2) in 15 ml of methylene chloride. The reaction mixture is kept at 5° for a further 15 minutes and is then kept at room temperature for 2 hours. The DCU which has precipitated is filtered off and the filrate is evaporated. For purification, the residue is recrystallised three times from ethyl acetate (12 ml) and petroleum ether (60 ml); melting point 88°–93.5° (decomposition). (DCU=dicyclohexylurea)
TLC:
[chloroform/methanol (85:15)] $R_f 0.72$

[toluene/acetone (7:3)] $R_f$ 0.44

Stage 12.4

Z-Thr(But)-Phe-Gaba-OTmse

A solution of 3.93 g of H-Phe-Gaba-OTmse [obtained from 5.42 g of Z-Phe-Gaba-OTmse (stage 12.3) by hydrogenation analogously to stage 12.2] and 5.45 g of Z-Thr(But)-ONSu in 25 ml of dimethylformamide is kept at room temperature for 15 hours, 0.34 ml of dimethylamino propylamine is added and the mixture is left to stand at room temperature for a further hour. The reaction mixture is evaporated under a high vacuum, the residue is dissolved in about 200 ml of ethyl acetate and the solution is washed with three times 30 ml of a 5% aqueous soluion of tartaric acid and with three times 30 ml of water. The organic phase, which is dried over sodium sulphate, is evaporated in vacuo and the residue is recrystallised twice from ethyl acetate (10 ml)/petroleum ether (80 ml); melting point 114°–117° (decomposition).
TLC:

[chloroform/methanol (85:15)] $R_f$ 0.75
[carbon tetrachloride/ethyl acetate (6:4)] $R_f$ 0.39

Stage 12.5

Z-Lys(Boc)-Thr(But)-Phe-Gaba-OTmse

A solution of 1.25 g of DCCI in 5 ml of methylene chloride is added, at 0°–5°, to a solution of 2.37 g of H-Thr(But)-Phe-Gaba-OTmse [obtained from 3.00 g of Z-Thr(But)-Phe-Gaba-OTmse by hydrogenation analogously to stage 12.2], 1.96 g of Z-Lys(Boc)-OH and 0.70 g of N-hydroxybenzotriazole in 10 ml of methylene chloride. After 15 minutes at 0°–5°, the mixture is kept at room temperature for 15 hours. The dicyclohexylurea which has precipitated is filtered off, the filtrate is evaporated in vacuo and the residue is recrystallised three times from ethyl acetate (20 ml)/petroleum ether (100 ml).
TLC:

[chloroform/methanol (85:15)] $R_f$ 0.73
[chloroform/methanol/water (14:6:1)] $R_f$ 0.87

Stage 12.5A

Bpoc-Phe-[D-Trp(NO₂)]-OH

A suspension of 0.50 g of 6-nitro-D-tryptophan and 1.10 g of Bpoc-Phe-ONSu in 10 ml of a mixture of dimethylformamide/water (8:2) is treated at room temperature with 0.1 N sodium hydroxide solution so that the pH remains at a value of 7.5. After 2.5 hours, the total consumption of sodium hydroxide solution is 31.5 ml. The reaction mixture is cooled to 0°–5° and 3.5 ml of 1 N hydrochloric acid are added slowly. The crude product which has precipitated is filtered off, dried and twice chromatographed through a silica gel column (60 g of adsorbent in each case) using a mixture of chloroform/methanol (85:15) and carbon tetrachloride/ethyl acetate (6:4) as the eluent.
TLC:

[chloroform/methanol (85:15)] $R_f$ 0.12
[chloroform/methanol/water (14:6:1)] $R_f$ 0.50

Stage 12.6

Bpoc-Phe-[D-Trp(NO₂)]-Lys(Boc)-Thr(But)-Phe-Gaba-OTmse

A solution of 0.36 g of DCCI in 2 ml of methylene chloride is added, at 0°–5°, to a solution of 1.08 g of H-Lys(Boc)-Thr(But)-Phe-Gaba-OTmse [obtained from 1.30 g of Z-Lys(Boc)-Thr(But)-Phe-Gaba-OTmse (stage 12.5) by hydrogenation analogously to stage 12.2], 0.93 g of Bpoc-Phe-[D-Trp(NO₂)]-OH (stage 12.5A) and 0.22 g of N-hydroxybenzotriazole in 8 ml of methylene chloride. After 15 minutes at 0°–5°, the mixture is kept at room temperature for 4 hours. For working up, the dicyclohexylurea which has precipitated is filtered off, the filtrate is evaporated in vacuo and the residue is reprecipitated from a mixture of ethyl acetate (10 ml) and petroleum ether (70 ml) and then ground with methanol (10 ml).
TLC:

[toluene/acetone (7:3) $R_f$ 0.20
[chloroform/methanol/water (14:6:1)] $R_f$ 0.90

Stage 12.7

HCl.H-Phe-[D-Trp(NO₂)]-Lys(Boc)-Thr(But)-Phe-Gaba-OTmse

A solution of 1.27 g of Bpoc-Asn-Phe-Phe[D-Trp(NO₂)]-Lys(Boc)-Thr(But)-Phe-Gaba-OTmse (stage 12.6) in a mixture of 27 ml of trifluoroethanol and 3 ml of water is kept at an apparent pH of 1.5 (glass electrode, automatic titration apparatus) by gradually adding a mixture of trifluoroethanol and concentrated hydrochloric acid (9:1). By the time the reaction is complete, about 0.76 ml of the reagent is consumed in the course of 1.5 hours at room temperature. The crude product obtained after evaporating in vacuo is stirred for one hour with 30 ml of ether and is then filtered off.
TLC:

[chloroform/methanol (85:15)] $R_f$ 0.55

Stage 12.7A

2-Trimethylsilylethyl-N-hydroxy-succinimidocarbonate (SEOC-ONsu)

62.6 g of N-methylmorpholine are added dropwise in the course of 15 minutes, at 0°–5°, to a solution of 100 g of chloroformic acid N-hydroxysuccinimide-ester and 73.2 g of 2-trimethylsilylethanol in 160 ml of methylene chloride. The mixture is stirred at 0°–5° for 2 hours and, for working up, 1 liter of ether is added and the mixture is washed with twice 200 ml of 1 N HCl, twice 200 ml of water, twice 200 ml of 5% sodium bicarbonate solution and three times 200 ml of water. The aqueous phases are post-extracted with 0.5 liter of ether and the combined organic phases are dried over sodium sulphate and evaporated. The residue is recrystallised from 360 ml of diisopropyl ether and the resulting crystals are filtered off and washed with 150 ml of hexane; melting point 101°–102°.

Stage 12.7B

SEOC-Asn-OH

The pH of a solution of 2.64 g of L-asparagine in 80 ml of a mixtutre of dimethylformamide/water (6:2) is adjusted to 7.5 by adding 0.21 ml of 1 N sodium hydroxide solution, and a solution of 5.19 g of SEOC-ONSu (stage 12.7A) in 10 ml of dimethylformamide is then added dropwise in the course of one hour, the pH of 7.5 being maintained continuously by adding further amounts of 1 N sodium hydroxide solution by means of an automatic titration apparatus. After 2.5 hours, a small amount of undissolved material is filtered off and dilute hydrochloric acid is added to the filtrate in an amount which is equivalent to the amount of 1 N sodium hydroxide solution consumed (about 20 ml). The solution is evaporated under a high vacuum and the residue is ground with 30 ml of cold water and filtered off; melting point 144.5°–146.5° (decomposition).
TLC: [chloroform/methanol/water (14:6:1)] $R_f$ 0.15

Stage 12.7C

SEOC-Asn-ONSu 0.79 g of N-hydroxy-succinimide is added to a solution of 1.72 g of SEOC-Asn-OH (stage 12.7B) in a mixture of 20 ml of ethyl acetate and 10 ml of dimethylformamide, and 1.54 g of DCCI are added to the solution, which is cooled to 0°–5°. After 2 hours at 0°–5°, the dicyclohexylurea which has precipitated is filtered off and the filtrate is diluted with 150 ml of ethyl acetate and washed with three times 50 ml of 1% oxalic acid solution and with four times 50 ml of water. The organic phase is dried over sodium sulphate and evaporated in vacuo; the resulting foam is used for the next stage without further purification.
TLC:

[chloroform/methanol/water (14:6:1)] $R_f$ 0.75

Stage 12.7D

SEOC-Asn-Phe-OH

1 N Sodium hydroxide solution is added dropwise to a suspension of 0.64 g of phenylalanine and 1.44 g of SEOC-Asn-ONSu (stage 12.7C) in a mixture of 5 ml of dimethylformamide and 5 ml of water over a period of half an hour, at room temperature, by means of an automatic titration apparatus at a rate such that the pH of 7.5 is maintained. For working up, a small amount of undissolved material is filtered off, dilute hydrochloric acid is added to the filtrate, at 0°–5°, in an amount (about 4.2 ml of a 1 N solution) which is equivalent to the amount of sodium hydroxide consumed. The crude product which has precipitated is dried over phosphorus pentoxide and recrystallised from 40 ml of ethyl acetate; melting point 156°–158° (decomposition).
TLC:

[chloroform/methanol/water (14:6:1)] $R_f$ 0.33

Stage 12.8

SEOC-Asn-Phe-Phe-[D-Trp(NO₂)]-Lys(Boc)-Thr(But)-Phe-Gaba-OTmse

A solution of 500 mg of HCl.H-Phe-[D-Trp(NO$_2$)]-Lys(Boc)-Thr(But)-Phe-Gaba-OTmse (stage 12.7), 202 mg of SEOC-Asn-Phe-OH (stage 12.7D), 65 mg of N-hydroxybenzotriazole and 44 mg of N-methylmorpholine in 5 ml of dimethylformamide is cooled to 0°, 116 mg of DCCI are added and the mixture is kept at 0°–5° for 15 minutes and at room temperature for 6 hours. The dicyclohexylurea which has precipitated is filtered off, the filtrate is evaporated under a high vacuum and the residue is ground with 20 ml of water and filtered off with suction. The crude product is ground a further twice with, in each case, 4 ml of methanol and filtered off.
TLC:

[chloroform/methanol (85:15)] $R_f$ 0.80
[chloroform/methanol/water (14:6:1)] $R_f$ 0.90

Stage 12.9

H-Asn-Phe-Phe-[D-Trp(NO₂)]-Lys(Boc)-Thr(But)-Phe-Gaba-OH 530 mg of SEOC-Asn-Phe-Phe-[D-Trp(NO$_2$)]-Lys(Boc)-Thr(But)-Phe-Gaba-OTmse (stage 12.8) are dissolved in 46.7 ml of a freshly prepared, anhydrous 0.15 M solution of tetraethylammonium fluoride in dimethylformamide and the solution is kept at room temperature for one hour. The solution is cooled to 0°–5°, 0.70 ml of aqueous 1 N hydrochloric acid is added, with good stirring, and the mixture is concentrated to 3 ml under a high vacuum. The product is precipitated by adding 30 ml of water.
TLC:

[chloroform/methanol/water (14:6:1)] $R_f$ 0.45

Stage 12.10

⌐ Asn—Phe—Phe—[D-Trp(NO₂)]—Lys(Boc—Thr(But)—Phe—Gaba ⌐

In a manner analogous to that described in Example 1, H-Asn-Phe-Phe-[D-Trp(NO$_2$)]-Lys(Boc)-Thr(But)-Phe-Gaba-OH (stage 12.9) is obtained by cyclisation by means of DCCI and N-hydroxybenzotriazole. The crude product is purified by counter-current partitioning (K=1.08).
TLC:

[chloroform/methanol (85:15)] $R_f$ 0.45
[chloroform/methanol/water (14:6:1)] $R_f$ 0.60

EXAMPLE 13

⌐ Asn—Phe—Phe—[Trp(Br)]—Lys—Thr—Phe—Gaba ⌐

(The symbol [Trp(Br)] denotes 5-bromo-L-tryptophan.)

The synthesis of the title compound is carried out under the same conditions as the synthesis in the preceding Example 12, except that 5-bromo-L-tryptophan is used in place of 6-nitro-D-tryptophan in corresponding starting materials and intermediates. Counter-current partitioning: 320 stages, K=9.0.
TLC:
System 101: $R_f$ 0.60
System 111B: $R_f$ 0.40
112A: $R_f$ 0.52
The starting material of the formula ⌐ Asn—Phe—Phe—[Trp(Br)]—Lys(Boc)—Thr(But)—Phe—Gaba ⌐ is obtained as follows.

Stage 13.1

Bpoc-Phe-[Trp(Br)]-OH

In a manner analogous to that described in Example 12.5A, 0.57 g of 5-bromo-L-tryptophan is reacted with 1.00 g of Bpoc-Phe-ONSu.
TLC:

[chloroform/methanol (85:15)] $R_f$ 0.15
[chloroform/methanol/water (14:6:1)] $R_f$ 0.55

Stage 13.2

Bpoc-Phe[Trp(Br)]-Lys(Boc)-Thr(But)-Phe-Gaba-OTmse

A mixture of 0.57 g of Bpoc-Phe-[Trp(Br)]-OH (stage 13.1), 0.63 g of H-Lys(Boc)-Thr(But)-Phe-Gaba-OTmse (Example 12.5), 0.13 g of N-hydroxybenzotriazole and 0.21 g of DCCI is reacted in a manner analogous to that in Example 12.6. For purification, the crude product is dissolved in 10 ml of hot methanol and precipitated by cooling.
TLC:
[chloroform/methanol (85:15)] $R_f$ 0.80
[chloroform/methanol/water (14:6:1)] $R_f$ 0.90

Stage 13.3

HCl.H-Phe-[Trp(Br)]-Lys(Boc)-Thr(But)-Phe-Gaba-OTmse 0.84 g of Bpoc-Phe-[Trp(Br)]-Lys(Boc)-Thr(But)-Phe-Gaba-OTmse is treated analogously to Example 12.7.
TLC:
[chloroform/methanol (85:15)] $R_f$ 0.65
[chloroform/methanol/water (14:6:1)] $R_f$ 0.90

Stage 13.4

SEOC-Asn-Phe-Phe-[Trp(Br)]-Lys(Boc)-Thr(But)-Phe-Gaba-OTmse

Analogously to Example 12.8, 700 mg of HCl.H-Phe-[Trp(Br)]-Lys(Boc)-Thr(But)-Phe-Gaba-OTmse (stage 13.3) and 250 mg of SEOC-Asn-Phe-OH (Example 12.7D) are coupled by means of 146 mg of DCCI in the presence of 88 mg of N-hydroxybenzotriazole and 60 mg of N-methylmorpholine.
TLC:
[chloroform/methanol (85:15)] $R_f$ 0.77
[chloroform/methanol/water (14:6:1)] $R_f$ 0.85

Stage 13.5

H-Asn-Phe-Phe-[Trp(Br)]-Lys(Boc)-Thr(But)-Phe-Gaba-OH

Analogously to Example 12.9, the SEOC and the Tmse groups in 500 mg of SEOC-Asn-Phe-Phe-[Trp(Br)]-Lys(Boc)-Thr(But)-Phe-Gaba-OTmse (stage 13.4) are detached simultaneously.
TLC:
[chloroform/methanol/water (14:6:1)] $R_f$ 0.50

Stage 13.6

└─Asn—Phe—Phe—[Trp(Br)]—Lys(Boc)—Thr(But)—Phe—Gaba─┘

Cyclisation of H-Asn-Phe-Phe-[Trp(Br)]-Lys(Boc)-Thr(But)-Phe-Gaba-OH by means of DCCI and N-hydroxybenzotriazole in accordance with the process described in Example 1.10 yields a crude product, which is purified by counter-current partitioning (K=0.86).
TLC:
[chloroform/methanol (85:15)] $R_f$ 0.06
[chloroform/methanol/water (14:6:1)] $R_f$ 0.85

EXAMPLE 14

└─Asn—Phe—Phe—(D-Trp)—Lys—Thr—[Phe(J)]—Gaba─┘

Analogously to Example 1, 130 mg of

└─Asn—Phe—Phe—(D-Trp)—Lys(Boc)—Thr—[Phe(J)]Gaba─┘ are treated with trifluoroacetic acid and the product is converted to the acetate by means of an ion exchanger. Purification is effected by counter-current partitioning in the same system as indicated in Example 1; K=9.
TLC: (silica gel Merck); System 157C: $R_f$ 0.25 (The symbol Ph(J) denotes p-iodo-L-phenylalanine.)
The starting material is obtained as follows:

Stage 14.1

Z-(D-Trp)-Lys(Boc)-Thr-OMe 0.56 ml of N-methylmorpholine and 1.03 g of DCCI are added, at −5°, to a solution of 2.78 g of Z-(D-Trp)-Lys(Boc)-OH (Example 1.3A), 0.85 g of H-Thr-OMe hydrochloride and 0.77 g of N-hydroxybenzotriazole in 16 ml of acetonitrile. After 15 hours at −5°, the mixture is worked up analogously to stage 14.3B. The product is recrystallised from ethyl acetate/hexane; melting point: 120°–122°.
TLC: System 157A: $R_f$ 0.47

Stage 14.1A

SEOC-Asn-Phe-Phe-OH

A solution of 2.24 g of Z-Asn-Phe-Phe-OH in 40 ml of dimethylformamide is hydrogenated, with the addition of 0.23 g of Pd-on-charcoal (10%), at room temperature for 4 hours. After filtering off the catalyst, the solution is concentrated to about 5 ml under a high vacuum and is further processed direct in this form. 10 ml of water are added to a solution of 1.71 g of resulting H-Asn-Phe-Phe-OH in 15 ml of dimethylformamide and, after adding 1.04 g of SEOC-ONSu, the resulting suspension is kept at a pH of 7.5 for 2 hours (room temperature) by gradually adding 2 N sodium hydroxide solution by means of an automatic titration apparatus. After a further addition of 1.04 g of SEOC-ONSu, the mixture is left at pH 7.5 for a further 4 hours. For working up, the small amount of undissolved material is filtered off from the solution, hydrochloric acid is added to the filtrate, at 0°–5°, in an amount equivalent to the amount of sodium hydroxide consumed (about 8.0 ml of 2 N solution) and the product which has precipitated is filtered off and dried. The crude product is recrystallised once from 10 ml of methanol with 100 ml of ether and once from 10 ml of methanol with 80 ml of water; melting point 176°–182° (decomposition).
TLC:
[chloroform/methanol/water (14:6:1)] $R_f$ 0.30

Stage 14.2

SEOC-Asn-Phe-Phe-(D-Trp)-Lys(Boc)-Thr-OMe

A solution of 340 mg of Z-(D-Trp)-Lys(Boc)-Thr-OMe (stage 14.1) in a mixture of 15 ml of methanol and water (9:1) is hydrogenated at pH 4.5 in the presence of 50 mg of palladium-on-charcoal (10%) and with the addition of 0.2 N hydrochloric acid in the same solvent. After filtering off the catalyst, the filtrate is concentrated in vacuo and then twice evaporated with dimethylformamide. 285 mg of SEOC-Asn-Phe-Phe-OH (stage 14.1A) and 90 mg of N-hydroxybenzotriazole are added to the residual solution (total 1.5 g). 0.056 ml of N-methylmorpholine and 123 mg of DCCI are added at −5° and the mixture is left to stand for 18 hours at −5°. Working up is carried out analogously to Example 7.1; the crude product is recrystallised from aqueous trifluoroethanol.

TLC: System 157A: $R_f$ 0.45

Stage 14.3

SEOC-Asn-Phe-Phe-(D-Trp)-Lys(Boc)-Thr hydrazide 0.16 ml of hydrazine hydrate is added at room temperature to a solution of 355 mg of SEOC-Asn-Phe-Phe-(D-Trp)-Lys(Boc)-Thr-OMe (stage 14.2) in 1.1 ml of dimethylformamide. After 2½ hours, the solid mass is ground with 5 ml of water and the precipitate is filtered off with suction and washed with water until the hydrazine has been removed completely. The product obtained after grinding with methanol is a single compound.

TLC: System 157B: $R_f$ 0.25

Stage 14.3A

Boc-[Phe(J)]-OH 2.4 ml of di-tert.-butyl dicarbonate are added to a solution of 2.9 g of p-iodo-L-phenylalanine in 10 ml of 1 N sodium hydroxide solution and 25 ml of tert.-butanol and the mixture is stirred at room temperature for a further 3 hours and then left to stand for 20 hours. The reaction solution is partitioned between water and hexane; the organic phase is discarded and the aqueous phase is acidified, with ice-cooling, the product is taken up in ethyl acetate and the solvent is evaporated in vacuo. The product is purified by crystallisation from carbon tetrachloride; melting point 118°–120°.

TLC: System 157B: $R_f$ 0.35

Stage 14.3B

Boc-[Phe(J)]-Gaba-OTmse

A solution of 412 mg of DCCI in 1 ml of dimethylformamide is added, at +5°, to a solution of 406 mg of H-Gaba-OTmse (Example 12.2), 782 mg of Boc-[Phe(J)]-OH (stage 14.3A) and 306 mg of N-hydroxybenzotriazole in 5 ml of acetonitrile and 3 ml of dimethylformamide. After 20 hours at 5°, the dicyclohexylurea which has precipitated is filtered off and the filtrate is diluted with ethyl acetate and extracted by shaking with dilute hydrochloric acid and sodium bicarbonate solution. After drying over sodium sulphate, the solvent is evaporated and the product is recrystallised from hexane; melting point: 98°–100°.

TLC:
[cyclohexane/acetone (7:3)] $R_f$ 0.35
System 157A $R_f$ 0.68

Stage 14.3C

H-[Phe(J)]-Gaba-OTmse hydrochloride 1.5 ml of 1.2 N hydrochloric acid in a mixture of trifluoroethanol/water (9:1) are added to a solution of 345 mg of Boc-[Phe(J)]-Gaba-OTmse (stage 14.3B) in 0.7 ml of the same solvent. After 30 minutes, 10 ml of tert.-butanol are added to the mixture and the resulting mixture is concentrated in vacuo to about half its volume. This procedure is repeated a further three times and the residual tert.-butanol is then removed by lyophilisation. The residue is recrystallised from isopropanol/ether;

TLC: System 157C: $R_f$ 0.68

Stage 14.4

SEOC-Asn-Phe-Phe-(D-Trp)-Lys(Boc)-Thr-[Phe(J)]-Gaba-OTmse 0.14 ml of 5.3 N hydrochloric acid in dioxan and 0.04 ml of tert.-butyl nitrite are added, at −15° to −20°, to a solution of 320 mg of SEOC-Asn-Phe-Phe-(D-Trp)-Lys (Boc)-Thr hydrazide (stage 14.3) in 2 ml of dimethylformamide and the mixture is stirred for 15 minutes at this temperature. A solution of 193 mg of H-[Phe(J)]-Gaba-OTmse hydrochloride (stage 14.3C) in 0.5 ml of dimethylformamide and 0.18 ml of N-methylmorpholine is then added at −25°, the resulting mixture is warmed slowly to 0° and left to stand for 16 hours at this temperature. The product is precipitated by adding the reaction mixture dropwise to water and is purified by grinding with methanol and acetonitrile.

TLC:
[chloroform/trifluoroethanol/methanol (80:15:5)] $R_f$ 0.43

Stage 14.5

H-Asn-Phe-Phe-(D-Trp)-Lys(Boc)-Thr-[Phe(J)]-Gaba-OH 12.3 ml of a 0.34 M solution of tetraethylammonium fluoride in dimethylsulphoxide are added to a solution of 324 mg of SEOC-Asn-Phe-Phe-(D-Trp)-Lys(Boc)-Thr-[Phe(J)]-Gaba-OTmse (stage 14.4) in 2 ml of dimethylformamide and the mixture is left to stand at 30° for 1½ hours. The product is precipitated by adding the reaction mixture dropwise to 40 ml of ice-cold water which contains 0.41 ml of 1 N hydrochloric acid and after drying is used in the next stage.

TLC: System 157: $R_f$ 0.5

Stage 14.6

⌐ Asn—Phe—Phe—(D-Trp)—Lys(Boc)—Thr—[Phe(J)]Gaba ⌐

A solution of 258 mg of H-Asn-Phe-Phe-(D-Trp)-Lys (Boc)-Thr-[Phe(J)]-Gaba-OH, 300 mg of N-hydroxybenzotriazole and 410 mg of DCCI in 200 ml of dimethylformamide is left to stand at 50° for 20 hours. Working up and purification are carried out analogously to Example 8.2; K=1.1.

TLC: System 157A: $R_f$ 0.22

EXAMPLE 15

⌐ Asn—Phe—Phe—(D-Trp)—Lys—Thr—Tyr(But)—Gaba ⌐

0.7 ml of a 2.1 M solution of tetrabutylammonium fluoride in dimethylsulphoxide is added to a solution of 350 mg of

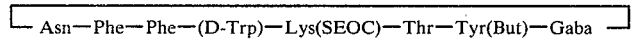

in 1.2 ml of dimethylformamide and the mixture is left to stand for 20 hours at 30°. After adding 20 ml of 1 N acetic acid and 50 ml of ethyl acetate, the aqueous phase is separated off, the organic phase is extracted twice more with a little water and the combined aqueous solutions are concentrated in vacuo and lyophilised. The residue, which consists of a mixture of product and tetrabutylammonium fluoride, is separated by preparative TLC on silica gel in system 157C. The product which is isolated from the silica gel and is not yet quite pure is purified by counter-current partitioning in the system chloroform/carbon tetrachloride/methanol/0.05 M ammonium acetate (9:1:7:3) over 460 stages. The pure product (K=0.9) is isolated in the customary manner.

TLC (silica gel Merck): System 157C: $R_f$ 0.25

The starting material is obtained as follows:

Stage 15.1

Z-(D-Trp)-Lys-OH trifluoroacetate 3.4 g of Z-(D-Trp)-Lys(Boc)-OH (Example 1.3A) are introduced into 34 ml of a mixture of trifluoroacetic acid/water (9:1) containing 0.5 ml of 2-mercaptoethanol, with ice-cooling, and, as soon as everything has dissolved, the solution is left to stand at 23° for a further 40 minutes. The crude product is precipitated by adding the reaction mixture dropwise to 400 ml of ether and 150 ml of hexane and is dissolved in 30 ml of water. After leaving to stand at room temperature for 18 hours, the solution is lyophilised and the residue is employed direct in the next stage.

TLC: System 157: $R_f$ 0.35

Stage 15.2

Z-(D-Trp)-Lys(SEOC)-OH 0.87 ml of triethylamine is added, at room temperature, to a solution of 3.0 g of Z-(D-Trp)-Lys-OH trifluoroacetate (stage 15.1) and 1.47 g of (2-trimethylsilylethyl)-(N-hydroxy)-succinimidocarbonate (Example 12.7A) in 5.2 ml of dimethylformamide and the mixture is left to stand for 15 hours. After diluting with ethyl acetate, the mixture is acidified to pH 1-2 with hydrochloric acid and the ethyl acetate solution is washed with water, dried over sodium sulphate and evaporated. The crude product is purified by countercurrent partitioning over 140 stages in the same system as described in Example 1.10; K=0.75.

TLC: System 157C: $R_f$ 0.55

Stage 15.3

Z-(D-Trp)-Lys(SEOC)-Thr-OMe 0.86 ml of N-methylmorpholine and 1.34 g of DCCI are added, at −5°, to a solution of 3.16 g of Z-(D-Trp)-Lys(SEOC)-OH (stage 15.2), 1.32 g of H-Thr-OMe hydrochloride and 0.95 g of N-hydroxybenzotriazole in 25 ml of acetonitrile and the mixture is left to stand for 16 hours at this temperature. The filtrate obtained after filtering off the dicyclohexylurea is diluted with ethyl acetate, washed with dilute hydrochloric acid and a sodium bicarbonate solution and dried over sodium sulphate. The residue obtained after evaporating the solvent is chromatographed on a silica gel column using mixtures of ethyl acetate/hexane (7:3) to (9:1). The fractions which are pure according to thin layer chromatography are evaporated to dryness.

TLC: System 157A: $R_f$ 0.38

Stage 15.4

Z-Asn-Phe-Phe-(D-Trp)-Lys(SEOC)-Thr-OMe

A solution of 1.31 g of Z-(D-Trp)-Lys(Boc)-Thr-OMe in 30 ml of methanol/water (95:5) is hydrogenated for 2 hours over 130 mg of palladium-on-charcoal (10%). After filtering off the catalyst, the filtrate is concentrated and twice evaporated with dimethylformamide under a high vacuum. 1.01 g of Z-Asn-Phe-Phe-OH (Example 1.5A) and 330 mg of N-hydroxybenzotriazole are added to the resulting solution, which contains 3.5 ml of dimethylformamide, the mixture is cooled to −5° and treated with a solution of 440 mg of DCCI in 0.5 ml of dimethylformamide and the resulting mixture is left to stand for 15 hours at 0° and worked up analogously to Example 7.1.

TLC: System 157A: $R_f$ 0.45

Stage 15.5

Z-Asn-Phe-Phe-(D-Trp)-Lys(SEOC)-Thr hydrazide 0.85 ml of hydrazine hydrate is added, at room temperature, to a solution of 2.0 g of Z-Asn-Phe-Phe-(D-Trp)-Lys(SEOC)-Thr-OMe in 6 ml of dimethylformamide. After 2.15 hours, the reaction mixture is worked up as in Example 14.3. Because it is exceptionally sparingly soluble, the product cannot be checked by TLC.

Stage 15.5A

Diethylammonium salt of Trt-Tyr(But)-OH 6.7 ml of water, 6.7 ml of diethylamine and, in the course of 30 minutes, with ice-cooling, 7.05 g of triphenylchloromethane are added to a solution of 4.0 g of H-Tyr(But)-OH in 50 ml of chloroform. After a further 1½ hours, the aqueous phase is separated off and the chloroform solution is extracted by shaking, twice with a 4% aqueous solution of diethylamine and twice with saturated sodium chloride solution, dried over sodium sulphate and freed from the solvent in vacuo. The residue is crystallised from ether/petroleum ether; melting point 141°–145°.

TLC: [toluene/acetone (1:1)] $R_f$ 0.48

Stage 15.5B

Trt-Tyr(But)-ONSu 4.7 g of the diethylammonium salt of Trt-Tyr(But)-OH (stage 15.5A) are shaken, with ice-cooling, with 100 ml of ethyl acetate and 10 ml of 0.5 M potassium sulphate solution and 10 ml of 0.5 M potassium bisulphate solution. After separating off the lower phase, the ethyl acetate solution is washed with water and dried over sodium sulphate and the solvent is distilled off gently in vacuo. The residue is dissolved in 50 ml of dimethylformamide, 1.1 g of N-hydroxysuccinimide and, at 0°, 1.94 g of DCCI are added and the mixture is left to stand at +5° for 15 hours. After filtering off the dicyclohexylurea, a crude product is precipitated from the filtrate with water and this product is chromatographed on a silica gel column with chloroform. The fractions which contain the product according to TLC are combined and recrystallised from methanol; melting point 163°–164°.

TLC: [chloroform/ethyl acetate (1:1)] $R_f$ 0.53

Stage 15.5C

Trt-Tyr(But)-Gaba-OBzl 0.77 ml of N-methylmorpholine is added to a suspension of 580 mg of Trt-Tyr(But)-ONSu (stage 15.5B) and 730 mg of H-Gaba-OBzl p-toluenesulphonate (Example 1.7A) in 1 ml of pure chloroform and the mixture is left to stand for 4 days at room temperature. After diluting with ethyl acetate, the solution is extracted by shaking, with ice-cooling, with 0.2 M potassium bisulphate solution and water, the organic phase is dried over sodium sulphate and the solvent is distilled off. The crude product is chromatographed on silica gel. The pure product is eluted with a mixture of ethyl acetate/hexane (1:1) and isolated in the customary manner.

TLC: [toluene/acetone (8:2)] $R_f$ 0.5

Stage 15.5D

H-Tyr(But)-Gaba-OBzl hydrochloride 1.2 N hydrochloric acid in a mixture of trifluoroethanol/water (9:1) is added by means of an automatic titration apparatus to a solution of 620 mg of Trt-Tyr(But)-Gaba-OBzl (stage 15.5C) in 20 ml of the same solvent, at pH 3.5, until no further acid is consumed. After adding 20 ml of tert.-butanol, the mixture is concentrated in vacuo. This is repeated twice more and the residual tert.-butanol is removed by lyophilisation. In order to remove triphenylcarbinol, the lyophilisate is partitioned between water and ether and the aqueous solution is then lyophilised.

TLC: System 157B $R_f$ 0.5

Stage 15.6

Z-Asn-Phe-Phe-(D-Trp)-Lys(SEOC)-Thr-Tyr(But)-Gaba-OBzl 0.47 ml of 4.6 N hydrochloric acid in dioxan and 0.11 ml of tert.-butyl nitrite are added, at −15° to −20°, to a solution of 975 mg of Z-Asn-Phe-Phe-(D-Trp)-Lys(-SEOC)-Thr hydrazide (stage 15.5) in 7 ml of dimethylformamide. After 15 minutes, a solution of 385 mg of H-Tyr(But)-Gaba-OBzl hydrochloride (stage 15.5D) in 0.5 ml of dimethylformamide and 0.44 ml of N-methylmorpholine is added, at −25°, to this reaction mixture and the mixture is left to stand for 15 hours at 0°. The product is precipitated with water and purified by grinding with acetonitrile and methanol. Because of the insolubility of the product, a TLC check cannot be carried out.

Stage 15.7

H-Asn-Phe-Phe-(D-Trp)-Lys(SEOC)-Thr-Tyr(But)-Gaba-OH

A solution of 1.1 g of Z-Asn-Phe-Phe-(D-Trp)-Lys (SEOC)-Thr-Tyr(But)-Gaba-OBzl in 30 ml of dimethylformamide is hydrogenated for 3 hours in the presence of 100 mg of palladium-on-charcoal (10%). The catalyst is filtered off with suction, the filtrate is concentrated and the product is precipitated with water. It is purified by dissolving in 5 ml of dimethylformamide and precipitating with 15 ml of methanol.

TLC: System 157: $R_f$ 0.55

Stage 15.8

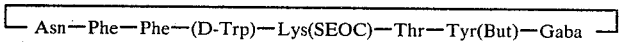

A solution of 700 mg of H-Asn-Phe-Phe-(D-Trp)-Lys (SEOC)-Thr-Tyr(But)-Gaba-OH (stage 15.7), N-hydroxybenzotriazole and 1.11 g of DCCI in 540 ml of dimethylformamide is cyclised at 50° for 21 hours. Working up is carried out analogously to Example 7.3. The product is purified by column chromatography over silica gel and the pure substance is eluted with a mixture of chloroform/trifluoroethanol/methanol (87:5:8).

TLC: System 157B: $R_f$ 0.38

EXAMPLE 16

(A) An injection solution containing 2.0 mg of the octapeptide

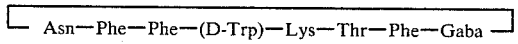

(designated "active ingredient" below) obtained according to Example 1 is obtained as follows:

1.0 mg of glacial acetic acid, 0.8 mg of sodium acetate, 8.0 mg of sodium chloride and 2.0 mg of active ingredient are dissolved in 0.7 ml of distilled water and the solution is made up to 1 ml with distilled water. The solution is heated for 20 minutes at 120° C. in an autoclave. After sterilisation, the pH is 4.5.

(B) An injection solution containing 0.5 mg of the active ingredient is obtained as follows:

0.5 mg of active ingredient is dissolved in 0.7 ml of physiological sodium chloride solution and the solution is acidified to pH 4.0 with 0.1 N hydrochloric acid. The solution is made up to 1 ml with distilled water and filtered to render it sterile.

The end products described in Examples 2 to 15 are used as the active ingredient in the same way.

EXAMPLE 17

(A) A gelatine-containing injection solution containing 0.1 mg of active ingredient (cf. Example 16) is obtained as follows:

An aqueous solution of the active ingredient, which has been filtered to render it sterile, is mixed under aseptic conditions with a sterile gelatine solution, which contains phenol as preservative, with warming, so that 1.0 ml of solution has the following composition:

| | | |
|---|---|---|
| active ingredient | 0.1 | mg |
| gelatine | 150.0 | mg |
| phenol | 4.7 | mg |
| distilled water to make up to | 1.0 | ml |

The mixture is filled under aseptic conditions into 1.0 ml phials.

(B) An analogous injection solution containing 0.5 mg of the active ingredient is obtained in the same way as indicated above by preparing a mixture of the following composition:

| active ingredient | 0.5 | mg |
|---|---|---|
| gelatine | 280.0 | mg |
| phenol | 5.0 | mg |
| distilled water to make up to | 1.0 | ml |

The mixture is filled under aseptic conditions into 1.0 ml phials.

EXAMPLE 18

A preparation containing 0.5 mg of active ingredient (cf. Example 16) as the sterile dry substance for injection is obtained as follows:

0.5 mg of active ingredient is dissolved in 1 ml of an aqueous solution of 20 mg of mannitol. The solution is filtered to render it sterile and is filled under aseptic conditions into a 2 ml ampoule, refrigerated and lyophilised. Before use, the lyophilisate is dissolved in distilled water. The solution is used intramuscularly or intravenously.

EXAMPLE 19

An injection preparation containing the active ingredient (cf. Example 16) in the form of a polyphosphate suspension is obtained as follows:

(A) With 1.0 mg of active ingredient:

A solution of 1.0 mg of active ingredient and 9.0 mg of sodium chloride in 0.5 ml of distilled water is mixed with a solution of 2 mg of sodium polyphosphate "Calgon N" in 0.5 ml of distilled water. The resulting suspension has the following composition:

| active ingredient | 1.0 mg |
|---|---|
| sodium polyphosphate ("Calgon N") | 2.0 mg |
| sodium chloride | 9.0 mg |
| distilled water to make up to | 1.0 ml |

The suspension has a pH of 6.9. It is suitable for intramuscular use.

(B) With 0.5 mg of active ingredient:

A suspension of the following composition is prepared in the same way as indicated above.

| active ingredient | 0.5 mg |
|---|---|
| sodium polyphosphate ("Calgon 322") | 1.0 mg |
| sodium chloride | 9.0 mg |
| distilled water to make up to | 1.0 ml |

The pH of the suspension is 5.9.

EXAMPLE 20

Injection preparation containing 0.3 mg of active ingredient (cf. Example 16) in the form of an oily aluminium stearate gel.

A 2% aluminium stearate gel is prepared in the customary manner by suspending 1.0 g of aluminium monostearate in 49.0 g of groundnut oil and then warming the suspension to 130° C. for 10 minutes. 15.0 mg of active ingredient are suspended with 0.3 g of the above aluminium stearate gel and the suspension is homogenised and diluted with the remainder of the aluminium stearate gel. The gel thus obtained has the following composition:

| active ingredient | 0.3 mg |
|---|---|
| aluminium monostearate | 20.0 mg |
| groundnut oil to make up to | 1.0 mg |

The oily aluminium stearate gel suspension is suitable for intramuscular use.

EXAMPLE 21

Injection preparation containing 0.5 mg of active ingredient (cf. Example 16) in the form of a depot suspension with dextran sulphate.

0.36 mg of acetic acid, 1.9 mg of sodium acetate trihydrate, 0.8 mg of sodium chloride and 0.5 mg of active ingredient are dissolved in 0.4 ml of distilled water and the solution is made up to 0.5 ml with distilled water. 0.5 ml of a 0.1% solution of dextran sulphate (molecular weight 500,000) is added to this solution, whereupon a homogeneous precipitate forms. The resulting suspension has the following composition:

| active ingredient | 0.50 mg |
|---|---|
| dextran sulphate, molecular weight 500,000 | 0.50 mg |
| acetic acid, 100% | 0.36 mg |
| sodium acetate trihydrate | 1.90 mg |
| sodium chloride | 8.00 mg |
| distilled water to make up to | 1.00 ml |

The aqueous suspension is suitable for intramuscular and subcutaneous injection.

EXAMPLE 22

Nasal Spray 30 mg of finely ground active ingredient (cf. Example 16) are suspended in a mixture of 75 mg of benzyl alcohol and 1.395 g of Miglyol 812. Aluminium monoblock cans (capacity 10 ml) are filled with this suspension, sealed with a metering valve and filled with 6.0 g of Freon 12/114 (40:60) under nitrogen pressure. The aluminium can, which has a net weight of, in total, 7.5 g, contains 100 single doses of 0.3 mg of active ingredient. The spray can is so set by means of the valve that one press releases a single dose as a spray.

Nasal sprays which in place of Miglyol contain the same amount of isopropyl myristate or isopropyl palmitate or "Labrafac WL 1219" (a mixture of glycerol esters and polyoxyethylene glycol esters of fatty acids having 8 and 10 carbon atoms) are prepared in the same way.

What is claimed is:

1. A cyclopeptide of the formula

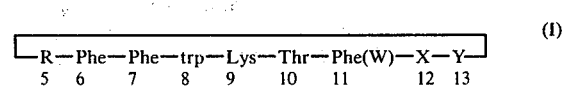

(I)

in which R is Asn, trp is D-Trp or L-Trp, which can be substituted in the benzene ring by halogen atoms or nitro groups, W is a free or etherified hydroxyl group or halogen atom present as a substituent on the benzene ring of the L-phenylalanine radical, or is hydrogen, X is the radical of an ω-amino-lower alkane-(mono or di)-carboxylic acid of the formula

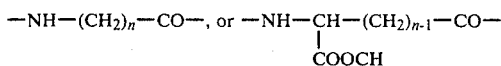

respectively in which n is an integer from 1 to 7 or de-X and Y is the radical of an ω-amino-lower alkane-(mono or di)-carboxylic acid as defined above or de-Y, or an acid addition salt or complex thereof.

2. The compound according to claim 1 of the formula I, in which R is Asn, trp is D-Trp or L-Trp, W is hydrogen, X is the radical of an ω-amino-lower alkane-monocarboxylic acid of the formula

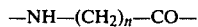

in which n is an integer from 2 to 4, or de-X and Y is the radical of an ω-amino-lower alkane-monocarboxylic acid as defined above or de-Y, or an acid addition salt or a complex thereof.

3. A compound according to claim 2, in which R is Asn, the tryptophan[8] radical has the D-configuration and —X—Y— together are —[Gaba]$_p$—, in which p is 0, 1 or 2.

4. A compound selected from the group consisting of a cyclic peptide of the formula

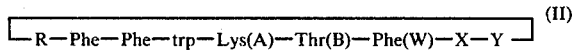

(II)

in which R is Asn, trp is D-Trp or L-Trp, which can be substituted in the benzene ring by halogen atoms or nitro groups, W is a free or etherified hydroxyl group or halogen atom present as a substituent on the benzene ring of the L-phenylalanine radical, or is hydrogen, X is the radical of an ω-amino-lower alkane-(mono or di)-carboxylic acid of the formula

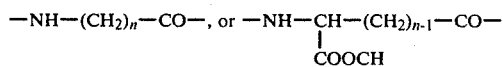

respectively in which n is an integer from 1 to 7 or de-X and Y is the radical of an ω-amino-lower alkane-(mono or di)-carboxylic acid or as defined above de-Y, A is an ε-amino protective group or hydrogen and B is a hydroxyl protective group or hydrogen, it being possible for only one of the symbols A and B to be hydrogen, and a corresponding linear piptide of the formula

H—[II']—C   (III)

in which II' is a radical corresponding to the formula II characterised above, in which the amide bond between any two adjacent aminoacid radicals of the peptide ring is interrupted, and C is a free hydroxyl group, a hydroxyl group modified by an activating group or the hydrazine group —NH—NH$_2$, and acid addition salts thereof.

5. A linear peptide according to claim 4, of the formula

H-R-Phe-Phe-trp-Lys(A)-Thr(B)-Phe-X-Y-C   (IIIc)

in which R is Asn, trp is D-Trp or L-Trp, X is the radical of an ω-amino-lower alkane-monocarboxylic acid of the formula

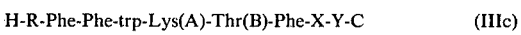

in which n is an integer from 1 to 7, or de-X and Y is the radical of an ω-amino-lower alkane-monocarboxylic acid as defined above or de-Y, A is an ε-amino protective group, B is a hydroxyl protective group and C is a free carboxyl group, or an acid addition salt thereof.

6. A compound characterised by the formula

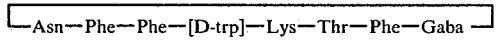

7. A compound characterised by the formula

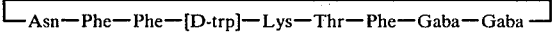

8. A compound characterised by the formula

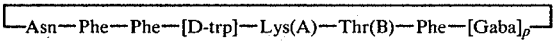

in which A is the tert.-butoxycarbonyl group and B is the tert.-butyl group and p is 1 or 2.

9. A pharmaceutical preparation for the treatment of excessive secretion of somatotrophin insulin and/or glucagon which contains an effective amount of at least one of the compounds characterised in any one of claims 3–9, 2 or 1 in combination or admixture with at least one inert, physiologically tolerable carrier and/or adjunct.

10. A method for the therapeutic treatment of excessive secretion of somatotropin, insulin and/or glucagon by administering a therapeutically effective dose of a compound characterised in any one of claims 3–7, 2 or 1.

* * * * *

UNITED STATES PATENT AND TRADEMARK OFFICE
CERTIFICATE OF CORRECTION

PATENT NO. : 4,238,481
DATED : December 9, 1980
INVENTOR(S) : Hans Rink et Al.

It is certified that error appears in the above-identified patent and that said Letters Patent are hereby corrected as shown below:

Claim 1, Column 45, Line 2 reads:

"$-NH-(CH_2)_n-CO-$, or $-NH-\underset{\underset{COOCH}{|}}{CH}-(CH_2)_{n-1}-CO-$".

Should now read:

"$-NH-(CH_2)_n-CO-$, or $-NH-\underset{\underset{COOH}{|}}{CH}-(CH_2)_{n-1}-CO-$".

Claim 4, Column 45, Line 51 reads:

"$-NH-(CH_2)_n-CO-$, or $-NH-\underset{\underset{COOCH}{|}}{CH}-(CH_2)_{n-1}-CO-$".

Should now read:

"$-NH-(CH_2)_n-CO-$, or $-NH-\underset{\underset{COOH}{|}}{CH}-(CH_2)_{n-1}-CO-$".

Signed and Sealed this

Seventeenth Day of March 1981

[SEAL]

*Attest:*

RENE D. TEGTMEYER

*Attesting Officer*    *Acting Commissioner of Patents and Trademarks*